(12) United States Patent
Feistel

(10) Patent No.: US 7,390,675 B2
(45) Date of Patent: *Jun. 24, 2008

(54) MULTI-FUNCTIONAL AND CONFIGURABLE ASSAY

(76) Inventor: Christopher Feistel, 255 Cypress Dr., No. 1, Laguna Beach, CA (US) 92651

( * ) Notice: Subject to any disclaimer, the term of this patent is extended or adjusted under 35 U.S.C. 154(b) by 314 days.

This patent is subject to a terminal disclaimer.

(21) Appl. No.: 11/106,949

(22) Filed: Apr. 15, 2005

(65) Prior Publication Data

US 2005/0239216 A1 Oct. 27, 2005

Related U.S. Application Data

(60) Continuation-in-part of application No. 10/068,040, filed on Feb. 5, 2002, now Pat. No. 6,991,912, which is a division of application No. 09/668,966, filed on Sep. 25, 2000, now Pat. No. 6,713,271, which is a continuation-in-part of application No. 09/418,864, filed on Oct. 15, 1999, now Pat. No. 6,136,549.

(51) Int. Cl.
*G01N 33/53* (2006.01)
(52) U.S. Cl. .................. 436/514; 436/518; 436/515; 436/807; 435/287.9
(58) Field of Classification Search .................. 436/518, 436/514, 515, 807; 435/287.9
See application file for complete search history.

(56) References Cited

U.S. PATENT DOCUMENTS

| | | | |
|---|---|---|---|
| 4,578,716 A | 3/1986 | van Rijckevorsel et al. | |
| 4,623,461 A * | 11/1986 | Hossom et al. | 210/445 |
| 4,731,337 A | 3/1988 | Luotola et al. | |
| 4,777,145 A | 10/1988 | Luotola et al. | |
| 4,935,147 A | 6/1990 | Ullman et al. | |
| 5,035,862 A | 7/1991 | Dietze et al. | |
| 5,075,078 A | 12/1991 | Osikowicz et al. | |
| 5,238,811 A | 8/1993 | Fujiwara et al. | |
| 5,252,459 A | 10/1993 | Tarcha et al. | |
| 5,384,264 A | 1/1995 | Chen et al. | |
| 5,508,164 A | 4/1996 | Kausch et al. | |
| 5,612,222 A | 3/1997 | Gordon et al. | |
| 5,643,722 A | 7/1997 | Rothschild et al. | |
| 5,712,170 A | 1/1998 | Kouvonen et al. | |
| 5,750,333 A | 5/1998 | Clark | |
| 5,770,388 A | 6/1998 | Vorpahl | |
| 5,800,994 A | 9/1998 | Martinelli et al. | |
| 5,817,458 A | 10/1998 | King et al. | |
| 5,821,073 A | 10/1998 | Lee | |
| 5,856,092 A | 1/1999 | Dale et al. | |

(Continued)

*Primary Examiner*—Bao-Thuy L Nguyen
(74) *Attorney, Agent, or Firm*—Stetina Brunda Garred & Brucker

(57) ABSTRACT

Novel magnetic assay methods and systems. According to a preferred embodiment, a chromatographic medium is provided that is designed to be contacted with a test solution having activated magnetic particles such that the solution flows bilaterally thereacross. A magnetic field, generated by a magnet or electromagnet, is selectively applied to the medium which causes the charged particles to become substantially bound at a site on the medium specified by the position of the magnet, to thus form a captured line or zone. In one preferred embodiment, the magnetic field is applied at the site on the medium at which the test solution is contacted. The assay is multi-configurable and can be modified to suit a particular immuno-separation procedure or application.

13 Claims, 10 Drawing Sheets

U.S. PATENT DOCUMENTS

| | | |
|---|---|---|
| 5,874,216 A | 2/1999 | Mapes |
| 5,876,935 A | 3/1999 | Pankratz et al. |
| 5,879,549 A | 3/1999 | Caiozza |
| 5,882,863 A | 3/1999 | Imai et al. |
| 5,888,748 A | 3/1999 | Crabb et al. |
| 5,922,537 A | 7/1999 | Ewart et al. |
| 5,925,573 A | 7/1999 | Colin et al. |
| 5,965,375 A | 10/1999 | Valkirs |
| 6,342,396 B1 | 1/2002 | Perrin et al. |
| 2002/0123074 A1 * | 9/2002 | Self et al. .................... 435/7.1 |

* cited by examiner

MULTI-FUNCTIONAL AND CONFIGURABLE ASSAY

CROSS-REFERENCE TO RELATED APPLICATIONS

The present application is a continuation-in-part of U.S. application Ser. No. 10/068,040, filed Feb. 5, 2002, now U.S. Pat. No. 6,991,912 SYSTEMS AND METHODS FOR PERFORMING MAGNETIC CHROMATOGRAPHY ASSAYS, which is a divisional patent application of U.S. patent application Ser. No. 09/668,966, filed Sep. 25, 2000, and now issued as U.S. Pat. No. 6,713,271 on Mar. 30, 2004, which was a continuation-in-part of U.S. patent application Ser. No. 09/418,864, filed Oct. 15, 1999, and now issued as U.S. Pat. No. 6,136,549, issued on Oct. 24, 2000.

STATEMENT RE: FEDERALLY SPONSORED RESEARCH/DEVELOPMENT

Not Applicable

BACKGROUND

Ligand-receptor assays or immunoassays are well-known in the art. Since their introduction in 1971, such assays have been utilized in a variety of applications to detect minute amounts of hormones, drugs, antibodies, and other substances suspected of being present in a given fluid sample. In this regard, researchers equipped with enzymes, antibodies, gene probes, and other reagents have made it possible to create chemical detection schemes for almost any compound of interest in a great diversity of applications. Among these applications are: commercial production of pharmaceuticals and food stuffs; food safety; diagnosis and treatment of disease in medical, veterinary, and agricultural environs; and detection and eradication of toxins in the environment. Common to all such applications is the requirement that chemical detection be performed in a timely, reliable, and cost effective manner.

Generally, bioassay schemes are developed and commercialized in formats suitable for use in laboratories equipped with general purpose instrumentation. Examples of these formats include immunoassay and DNA hybridization performed in test tubes, cuvettes, microtiter plates, columns, and electrophoretic gels. These formats usually include elaborate operational procedures and require frequent calibration using several calibrants which contain the analyte of interest at different concentrations. As a consequence, the high cost and complexity of operation associated with such formats limits widespread utilization thereof.

To address such drawbacks, developers and end users of immunoassays are increasingly replacing conventional bioassay formats which use test tubes, cuvettes, microtiter plates, columns, and electrophoretic gels with thin film chromatographic devices known as test strips. As is known in the art, the majority of test strips used for immunochemical detection of compounds are so called lateral flow test strips in which sample and reagents flow within the plane of the test strip. Advantageously, assays configured in a test strip format can produce rapid results, are simpler to operate, and are more cost-effective than conventional formats. Additionally, such test strip assays may be utilized by unskilled laborers and can produce results on-site (i.e., outside a laboratory facility).

Generally, such assays rely on the binding of analytes by receptors to determine the concentration of such analytes in a given sample and are typically characterized as either competitive or non-competitive. Non-competitive assays generally utilize receptors in substantial excess over the concentration of analytes to be determined in the assay. Typical of such non-competitive immunoassays include sandwich assays, which detect the presence of an analyte by binding two receptors thereto. In such arrangement, the first receptor, which is typically an antibody is bound to a solid phase such that when the analyte is present, such analyte becomes affixed thereto. A second receptor having a label covalently attached thereto, which may comprise a radioactive, fluorescent, enzymatic, dye or other detectable moiety (collectively referred to as tracers), is introduced to the assay which consequently binds to the bound ligand, to the extent the ligand is present, and thereafter produces a signal consistent with the presence of such ligand. If the sample does not contain the molecules of interest, the labeled receptor is carried past the immobilized receptor without reacting which, as a consequence, will not cause a change in the membrane. Such non-competitive immunoassays are primarily useful for the detection of large molecules such as proteins, large hormones or molecules which have multiple binding sites, such as human chorionic gonadotropin (HCG) and typically will not work with small molecules that have only one binding site.

Competitive assays, in contrast, generally involve competition between a ligand present in a given sample, and a ligand analog having a tracer/label covalently linked thereto to permit detection for a limited number of binding sites provided by the ligand receptor, which typically comprises an antibody bound to a solid phase. Such assays are particularly suited to detect smaller molecules, such as drugs and drug metabolites. In this context, drug analogs are utilized that have been covalently bound to a protein which is then immobilized on a membrane. Antibody specific to the drug is then labeled and immobilized on a porous pad. When a sample is added which is suspected of containing a given analyte, such sample dissolves the labeled antibody and carries it into contact with the immobilized drug-protein region. If there is little or no drug in the sample, a large amount of the labeled antibody is bound to the immobilized drug-protein region which, consequently, produces a detectable signal. If the sample contains a high amount of drug, little or no labeled antibody is bound to the immobilized drug-protein region and thus in turn gives little or no signal.

Today, rapid immunoassays generally consists of an adhesive-covered plastic backing onto which several porous pads and a piece of protein-binding membrane are attached. The membrane typically contains a section that has been impregnated with a binding partner (i.e., a receptor or ligand analog). A second pad is typically provided which contains a labeled target molecule or labeled antibody protein-binding membrane. When a sample suspected of containing a target ligand is contacted with the immunoassay, such sample dissolves the labeled element or tracer and the capillary action of the protein-binding membrane subsequently draws the sample with tracer dissolved therein into contact with the impregnated binding partner. When this reaction occurs, there is a change in the appearance of the binding membrane, with the difference providing a qualitative indication of the presence or absence of the ligand suspected of being present in such sample.

Typical examples of this form of test strip are those which visually display two parallel lines (known as capture lines) on a test membrane. Capture lines consist of immobilized capture reagents or receptors which are preapplied to the test membrane during its manufacture. In this regard, both virtually all prior art assays, whether competitive or non-competitive, typically deploy a receptor immobilized on a membrane, as assessed above. A schematic representation of the construction of a typical lateral flow test strip is as follows:

reagent pad//test membrane/capture line/test membrane/capture line/test membrane//absorbent pad.

where:

symbol/designates a phase boundary within a single chromatographic medium; and symbol//designates a union of two separate mediums (chromatographic or other medium).

One of the two capture lines serves as an indication that the test strip performance has not been compromised. In this regard, such capture line serves an important function by providing quality assurance and integrity of the assay, which is generally considered necessary insofar as individual test strip performance can vary greatly. The second of such capture lines becomes visible only when the sample contains an amount of analyte in excess of a minimum concentration (threshold concentration). Exemplary of such prior art systems and methodologies include the immunoassay systems and test strips disclosed in U.S. Pat. No. 5,658,723, issued on Aug. 19, 1997, to Oberhardt entitled IMMUNOASSAY SYSTEM USING FORCED CONVECTION CURRENTS and U.S. Pat. No. 5,712,170, issued on Jan. 27, 1998, to Kouvonen, et al. entitled TEST STRIP, ITS PRODUCTION AND USE, the teachings of each of which are expressly incorporated herein by reference.

Unfortunately, despite their cost-effectiveness and simplicity of use, typical test strip format assays are less accurate, less precise, and less sensitive to analyte presence than conventional formats. As a result of such drawbacks, the application of test strip format assays has been limited to semi-quantitative or qualitative assays. Among the more significant factors that contribute to the inaccuracy and imprecision of test strip format assays include the manufacture and use of capture lines. As is widely recognized, the manufacture of consistently uniform capture lines requires elaborate material control and manufacturing processes with rigid specifications that must operate within narrow tolerances. Moreover, to function properly, most test strip formats require that the analytes to be detected must be uniformly captured in a precise geometry at a precise location on the test strip and that factors such as the ambient humidity present at the time of test strip manufacture, type of membrane utilized in such manufacturing process, and a capture reagent-receptor itself contributing greatly to assay inaccuracies and false readings. A detailed discussion regarding the drawbacks associated with the binding of protein capture reagents in immunochromatographic assays can be found in Jones, Kevin D., "Troubleshooting Protein Binding in Nitrocellulose Membranes", Part I, IVD Technology, Volume V, No. II, March-April 1999, pages 32-41 and Part II, IVD Technology, Volume V, No. III, May-June 1999, pages 26-35, the teachings of which are expressly incorporated herein by reference.

Of further significant disadvantage is the fact that virtually all test strip format assays are formed to have a sequential, generally-linear configuration so as to facilitate the necessary lateral flow thereacross. Due to the fact that such fluid sample must necessarily migrate from its starting point across the reagent pad, the test membrane, and ultimately across the capture line(s) for detecting the presence of the suspect analyte, a substantial portion of the target analyte is often caused to become dispersed or otherwise inhibited from reaching the bound receptors forming the capture line. As such, a substantial portion of the target analyte sought to be detected can and frequently is missed altogether which can adversely affect the quantitative and qualitative results generated by such assays.

Such potential to inadvertently fail to detect the presence of a target analyte, whether it be through losing the target analyte sought to be detected or simply overlooking its presence is particularly problematic when attempting to detect the presence of cancer cells in a given fluid sample. For example, in a single 10 ml tube of blood, there are approximately fifty billion cells, and the presence of so much as one cancer cell among this cell population can be indicative of the presence of micrometastasis. Utilizing conventional screening techniques, such blood samples are typically processed to isolate the leukocytes present in such sample, which advantageously reduces such fluid sample for example, from 10 ml to between 1.0 to 0.5 ml, which consequently reduces the cell population from approximately fifty billion to approximately one hundred twenty million. Such procedure, however, typically results in the loss of cancer cells and as such may inadvertently remove the cancer cells sought to be detected.

In order to screen for cancer cells, such resultant sample is then portioned and applied to many microscope slides at a ratio of approximately one million cells to each slide, via well-known procedures such as cytospin. As is known, each slide prepared represents another inadvertent loss of cancer cells. Each respective one of the slides must then be meticulously scanned using a microscope. In this respect, each slide is typically divided into four hundred magnified fields comprised of one square millimeter areas that are each reviewed. Typically, such scanning process takes on average a half hour per slide. As a result, to thoroughly examine the condensed population of a one hundred twenty million leukocytes present in one 10 ml blood sample results requires the examination of one hundred twenty slides, producing forty eight thousand images that must be examined over a sixty hour period. Accordingly, even to the extent prior art assay techniques are effective at labeling a target cell sought to be detected, the process by which such labeled cell is ultimately isolated and detected is inherently unreliable, tedious and time consuming.

It is therefore desirable to devise an alternative lateral flow device which can capture analyte at a precise location, and preferably at the starting point or point of contact at which the fluid sample is deposited. It would be likewise desirable to devise an alternative assay that can capture an analyte at such starting point or point of contact in a precise geometry without the use of preapplied capture lines. There is also a need for an assay that has greater sensitivity in reproducibility than prior art assays and methods and is likewise inexpensive, less labor intensive, relatively easy to manufacture, and capable of being utilized for a wide variety of applications. There is further a need for an assay that may capture prepared cell specimens directly onto microscopic slides and significantly reduce the time and number of required images to be produced therefrom, particularly with respect to the isolation and detection of cancer cells.

In addition to the foregoing, there is a substantial need in the art for an alternative assay that can be constructed in a variety of configurations to substantially enhance the ability of the assay to perform a specific application. In this regard, it would be exceptionally advantageous for an assay system that is operative to serve as a separations platform for use in not only isolating proteins and genes, but also performing such functions as isolation, sorting, interrogation, and subsequent expansion of propagation of live cells. Such multi-configurable assays would further advantageously be operative to handle small quantities of compounds and conserve sample volume, to thus conserve the consumption of rare materials, and further be operative to eliminate, where applicable, conventional ancillary separation componentry, such as microtiter plates, separation columns, and the like that can further easily be integrated with many existing image analysis systems. Still further, there is a need for such a system that is of relative low cost, easy to manufacture, and used as multi-component construction to thus enable the assay to be readily constructed or fashioned to optimally perform a specific type of separation procedure.

BRIEF SUMMARY

The present invention specifically addresses and alleviates to the above-identified deficiencies in the art. In this regard, the present invention pertains to several novel bioassay methodologies, chromatographic devices, and an optional multi-mode photometer/analyzer which together can perform bioassays with accuracy and precision like that of conventional laboratory formats while retaining the operational simplicity, rapid analysis, and cost-effectiveness like that of test strip formats. The chromatographic devices and novel bioassay methodologies of the present invention further minimize problems associated with the manufacture of test strips which incorporate preapplied capture lines and further, can enable an analyte to be detected in a fluid sample in a manner that efficiently conserves and isolates the analyte present in such sample. Moreover, multimode photometers, novel test strip devices, and unique chemical analysis methods of the present invention represent a versatile, cost effective, simple, and accurate system which can quantify the amount of a chemical substance present in a sample that has not heretofore been available via prior art bioassay test strips.

According to a first aspect of the present invention, there is provided a novel magnetic chromatography method which consists of the steps of contacting activated magnetic particles suspended in a reaction mixture with a chromatographic medium (e.g., test strip or chromatographic plate), and thereafter applying a magnetic field thereto. As the activated magnetic particles flow laterally within the plane of the medium they encounter the applied magnetic field. The applied magnetic field attracts the magnetic particles forming a magnetic barrier that selectively retains magnetic particles while allowing the reaction mixture to continue to flow laterally thereacross. In an embodiment particularly useful in performing cell capture assays, the reaction mixture with magnetic particles is contacted upon an intermediate portion of a chromatographic medium having a magnetic field applied at the point of contact. The reaction mixture is thus caused to flow bilaterally across the medium, with the magnetic particles having the analyte of interest complexed therewith being captured at the starting point, or point of sample introduction, thus conserving the amount of analyte in the reaction mixture that would otherwise become lost through reaction mixture flow.

As such, there is thus eliminated the conventional capture lines formed by bound receptors that are utilized in prior art immunoassays as well as analyte loss that can occur during the assay. In this regard, a capture line is in effect assembled during the assay, and preferably at the outset. Advantageously, the magnetic chromatography assay methods of the present invention allow test strips and the like to be manufactured without preapplied capture lines. However, the methods of the present invention also anticipate a magnetic chromatography test strip having both preapplied capture lines and capture lines formed during the bioassay using magnetic chromatography as may be desired for a specific application.

The novel methods of the present invention may further deploy one or more applied magnetic field source(s) applied to the chromatography test strip assembly to detect multiple spectrophotometric analysis. For example, a common bar magnet or magnetic strip can be attached to the test strip backing with adhesive at one or more locations. Alternately, the magnetic source can be external to the test strip assembly whereby the magnetic source is selectively positioned in close proximity with the test strip while magnetic particles flow laterally therewithin. In preferred embodiments of the present invention, the source of the applied magnetic field may comprise either permanent magnets or electromagnets.

The present invention further includes a novel magnetic chromatography test strip for performing a bioassay that conserves the amount of analyte sought to be detected in a reaction mixture by forming a capture line or zone at the point at which the reaction mixture is contacted with the test strip. According to a preferred embodiment, the test strip comprises an elongate backing having first and second ends and an intermediate portion disposed therebetween. Upon the intermediate portion are a first vertical mesh for facilitating vertical flow and second lateral mesh for facilitation lateral flow, the latter being disposed underneath the first mesh. On opposed sides of the lateral flow mesh are absorbent pads that, in use, cause the reaction mixture ultimately passing through the first and second meshes to flow bilaterally. Such strip further preferably includes at least one magnet that is positioned underneath the vertical flow mesh and second lateral flow mesh.

In use, a reaction mixture is sequentially caused to flow from the vertical flow mesh, to the lateral flow mesh, and ultimately to the first and second absorbent pads disposed on the opposed sides of the lateral flow mesh. Preferably, such reaction mixture is deposited upon the strip by means of a sample well. The applied magnetic field provided by the magnet attracts the magnetic particles having the analyte of interest complexed thereto, which thus causes the same to be selectively retained at the site of deposition while the remainder of the reaction mixture continues to flow thereacross and ultimately to the respective of the absorbent pads. Such test strips are particularly well suited for the detection and isolation of cells, such as cancer cells, bacteria and the like, which are otherwise difficult to identify and isolate through prior art methods.

To further accomplish the objectives of the present invention, as well as to enable the novel magnetic chromatography methods to be utilized in a wide variety of applications extending across genomics, microgenomics, proteomics, and cell isolation for use in target identification (e.g. organelle sorting, protein fractionation, or target validation e.g. protein isolation, immune assays, molecular analysis) there is further provided a multi-configurable assay system. According to a preferred embodiment, such multi-configurable assay systems comprise a housing defining an interior and having a sample well formed thereon into which a reaction mixture containing magnetic particles, along with any applicable reagents, are deposited. Optionally, absorbent pads will be disposed within the housing on opposed sides of the sample well to enhance bilateral flow of a reaction mixture deposited in the sample well. A base is provided that may be formed to be either permanently or detachably fastened beneath the housing for receiving the reaction mixture. The base will define a target area that is aligned with sample well so that substantially all the reaction mixture is concentrated upon a single locus. A magnetic source, which may be either separate from or attached to the base, is provided that is aligned with the target area and sample well and operative to apply a magnetic field thereto to thus attract and retain the magnetic particles present in the reaction mixture at the target area while allowing the remaining reaction mixture to flow laterally across the target area. As a consequence, the magnetic particles present in the reaction mixture that have a target analyte (e.g. cell, protein, gene) complexed therewith will thus be captured and retained at the point of introduction, which thus optimally minimizes potential migration of the target analyte.

In refinements of such assay, the base member will comprise a conventional slide that, once the analyte of interest is captured thereupon, can be viewed, handled and stored per conventional slide preparations. Alternatively, the base may have a mesh with or without gel preparation deposited upon the target area thereof for use in a variety of applications, such as initiating the growth of a cell culture or serving as a means to suspend receptors that will selectively bind to target analytes of interest. Additionally such gel preparation may be provided with other types of reagents and enzymes, such as digestive enzymes, to selectively cleave proteins or otherwise serve to facilitate a desired biochemical reaction. Per the aforementioned embodiments, the base may further be provided with one or more layers of mesh to thus facilitate the direction of the flow of the reaction mixture as well as enhance the ability of the analyte of interest to be captured at the target area.

By virtue of its ability to be multi-configurable, the assays of the present invention are operative to be utilized in any of a variety of isolation, sorting and interrogation applications. Exemplary of such applications include single slide bench, bench top use, small batch testing, automated batch processing and continuous high throughput screening. Such multi-configurable assay, by virtue of its versatility, is exceptionally effective in capturing and isolating target analytes, such as cells, proteins and genes, functionally and structurally in tact, even if the same are membrane bound, fragile, or of exceptionally small or large size. Likewise, the multi-conformable assays can be used for cell engineering and interrogation, cell engineering and expansion or propagation, cell resistance and interrogation and cell sorting and serial interrogation applications. Advantageously, in all such configurations, the assay systems of the present invention will remain closed systems which thus eliminate many of the handling steps of traditional methods, as well as permits the rapid and easy handling of specimens with minimal risk of material exposure to workers and/or contamination of the sample being processed.

There is further provided as part of the present invention a novel analyzer comprised of a multimode photometer which can measure front surface fluorescence, luminescence and reflectance at a single focal point on the test strips of the present invention. According to a preferred embodiment, the multimode photometer consists of a base and optical canopy which collectively define an optical tunnel into which at least one test strip may be disposed. The chamber may include a magnetic source or be designed to be placed in close proximity to a magnetic source such that the test strip having activated magnetic particles flowing laterally therewithin may be caused to become substantially bound at a specific site or sites upon the test strip. When so arranged, a light or radiation source may be focused upon the test strip disposed within the optical tunnel such that the light or radiation may be aligned with the magnetic source and the reflected or emitted light from the test strip analyzed for analyte presence. Light and radiation of differing wave lengths may be utilized to determine the presence of appropriate analytes as per conventional spectrophotometric analysis. Optical filters and photodetectors may further be deployed as may be necessary for a particular spectrophotometric application.

It is therefore an object of the present invention to provide a novel magnetic chromatography assay and method utilizing a test strip format that has greater sensitivity and reproducibility than prior art test strip assays.

Another object of the present invention is to provide a novel magnetic chromatography assay and method that utilizes a test strip format, but dispenses with a need to form a capture line by binding receptors to a test membrane.

Another object of the present invention is to provide a novel magnetic chromatography assay and method that can be arrayed in a test strip format and utilized to provide quantitative analysis.

Another object of the present invention is to provide a novel magnetic chromatography assay and method that can form a capture line at the point of contact where a reaction member comes into contact with such test strip.

Another object of the present invention is to provide a novel magnetic chromatography assay and method that can conserve the amount of analyte present in a reaction mixture by identifying and isolating the same at the initiation of the performance of such assay.

Another object of the present invention is to provide a novel magnetic chromatography assay and method that may be adapted to provide quantitative and qualitative analysis for multiple analytes.

Another object of the present invention is to provide a novel magnetic chromatography assay and method that is easy to use, of simple construction, and inexpensive to manufacture.

Another object of the present invention is to provide a novel magnetic chromatography assay and method that may be utilized to provide spectrophotometric analysis, including but not limited to, surface reflectance, surface fluorescence, and surface luminescence.

Another object of the present invention is to provide a novel magnetic chromatography assay and method which may be configured to isolate target cells and facilitate the ability to detect the same.

Another object of the present invention is to provide a novel magnetic chromatography assay and method which may be adapted to capture cells directly onto slides and facilitate microscopic examination thereof.

Another object of the present invention is to provide a novel magnetic chromatography assay and method which may be configured to perform individual sample analysis, batch sample analysis, and linear-array analysis.

Another object of the present invention is to provide a novel magnetic chromatography assay system that is multi-configurable and capable of being utilized in a wide variety of applications.

Another object of the present invention is to provide a novel magnetic chromatography assay system that can permit efficient handling of small or large numbers of specimens, and is readily scaleable from single slide bench top applications to a continuous high throughput screening environment.

Another object of the present invention is to provide a novel magnetic chromatography assay system that is operative to rapidly isolate and sort sub-populations of cells with specific antigenic expression, and can further optionally be useful in facilitating cell expansion/propagation.

Another object of the present invention is to provide a novel magnetic chromatography assay system that is readily configurable to perform assays related to cell isolation, creation of a cell culture, cell engineering, cell resistance and cell sorting and serial interrogation.

Another object of the present invention is to provide a novel magnetic chromatography assay system that can substantially reduce, if not eliminate, reliance on microtiter plates, separation columns and the need to perform cell transfer procedures while at the same time achieving greater cellular capture and minimizing cell losses.

Another object of the present invention is to provide a novel magnetic chromatography assay system that eliminates many of the handling steps of traditional assay methods and further permits the rapid and easy handling of specimens with minimal risk of bacterial exposure to workers and/or contamination of the sample being processed.

Another object of the present invention is to provide a novel magnetic chromatography assay system that provides structure for performing post-assay assessment and manipulation, including but not limited to cellular testing, lysing and/or protein/organelle isolation and separation.

Another object of the present invention is to provide a novel magnetic chromatography assay and method wherein such assay may be configured to be reusable or disposable.

Another object of the present invention is to provide a novel magnetic chromatography assay and method which will accommodate conventional reagents prepackaged in unit doses.

Another object of the present invention is to provide a novel magnetic chromatography assay and method that can be used for quantitative, semi-quantitative, and qualitative immunoassay of analytes and DNA hybridization assays.

Another object of the present invention is to provide an optical analyzer consisting of a multimode photometer for performing spectrophotometric analysis, including but not limited to, surface reflectance, surface fluorescence, and surface luminescence.

Another object of the present invention is to provide an analyzer consisting of a multimode photometer which is of simple construction, easy to utilize, and may be configured to perform individual sample analysis, batch sample analysis, and linear-array analysis.

Another object of the present invention is to provide an analyzer consisting of a multimode photometer that, when utilized in conjunction with the magnetic chromatography assays of the present invention, may be utilized to quantify the amount of a given analyte at a fixed location on a test strip assay, irrespective of orientation of such assay and lateral flow of reaction mixture utilized therewith.

BRIEF DESCRIPTION OF THE DRAWINGS

These as well as other features of the present invention, will become more apparent upon reference to the drawings wherein:

FIG. 1b is an exploded view of the components comprising the assay test strip depicted in FIG. 1a.

FIG. 1c is a side view of the assay depicted in FIG. 1a.

FIG. 2b is a side view of the assay test strip depicted in FIG. 2a.

FIG. 6b is a side view of the test strip depicted in FIG. 6a.

FIG. 7b is a side view of the assay test strip depicted in FIG. 7a.

DETAILED DESCRIPTION

The following detailed description and the accompanying drawings are provided for the purpose of describing certain presently preferred embodiments of the invention only, and are not intended to limit the scope of the claimed invention in any way. In this regard, there is disclosed herein a novel assay system and method that, unlike prior art assay systems, and in particular test strip assays, can quantitatively and qualitatively detect the presence of an analyte, control, calibrator, or combination thereof in a given fluid sample with extraordinary precision and reproducibility. Moreover, the novel assays and methods of the present invention provide all of the advantages associated with conventional test strips assays insofar as the same need not undergo remote analysis at a laboratory facility and further, do not require handling by trained professionals. There is further provided a novel analyzer, which comprises a multimode photometer, is useful in conducting spectrophotometric analysis in conjunction with the assays and methods of the present invention.

Figure 1A:
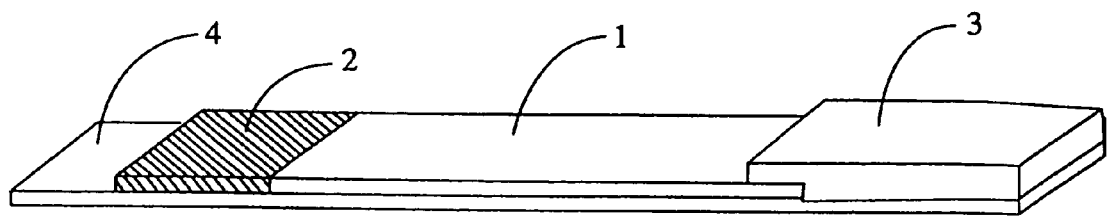
FIG. 1a is a perspective view of an assay test strip for using the practice of the methods of the present invention, said test strip being constructed in accordance to a first preferred embodiment.
Figure 1B:
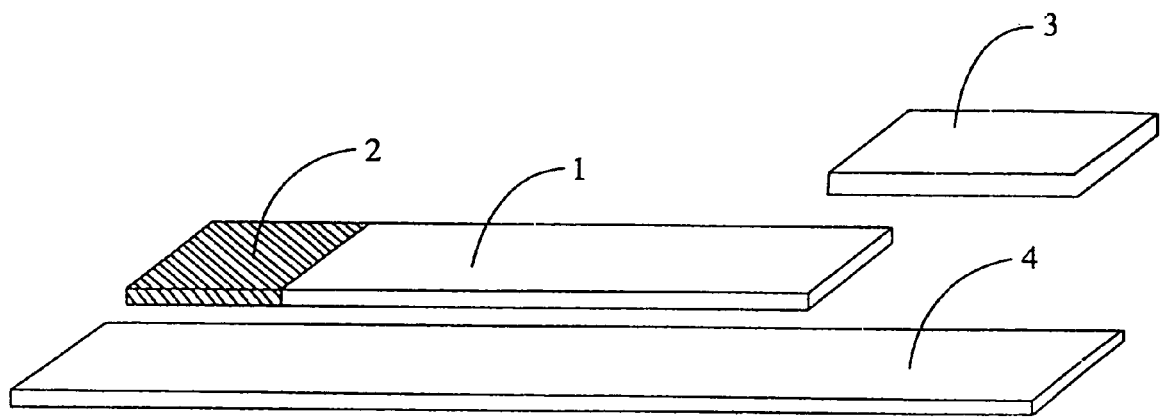
Figure 1C:
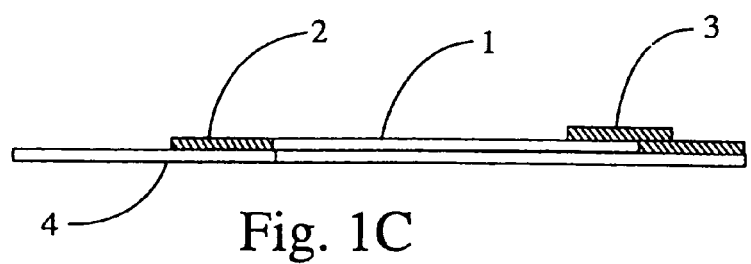

Referring now to the drawings, initially to FIGS. 1a-1c, there is shown a preferred embodiment of a test strip for use in magnetic chromatography. The test strip is comprised of a test membrane 1 having a reagent zone 2 at its one end and an absorbent pad 3 at its other end. These components are attached to a backing 4 made of plastic, glass or other suitably rigid material. Similar to prior art test strips, the test strip is simple to manufacture by lamination.

Figure 2A:
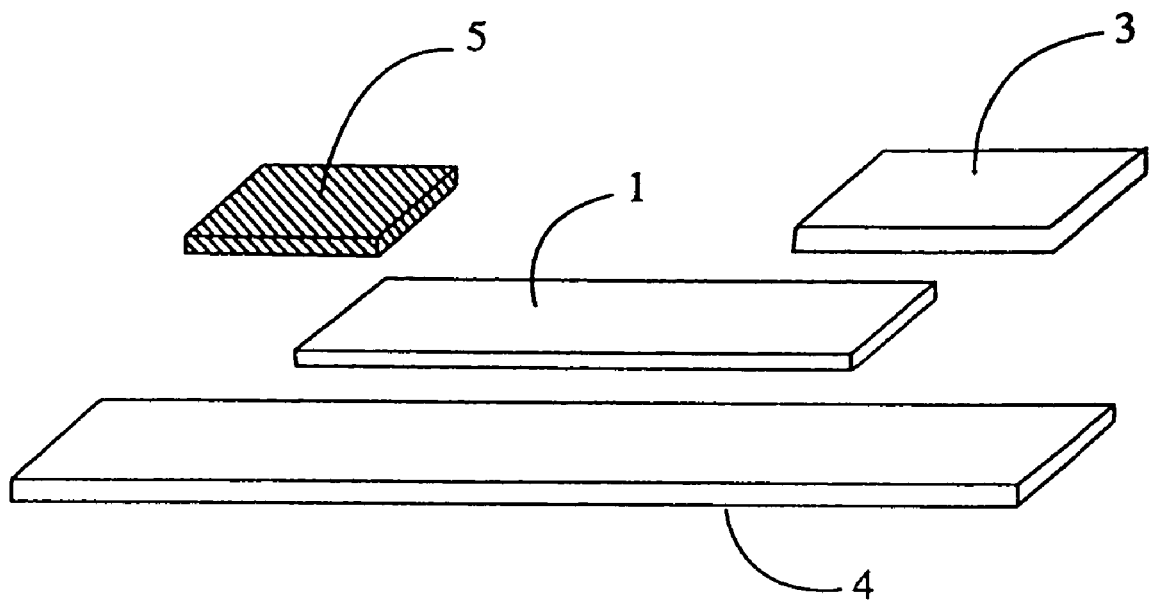
FIG. 2a is an exploded perspective view of an assay test strip constructed in accordance with a second preferred embodiment of the present invention.
Figure 2B:
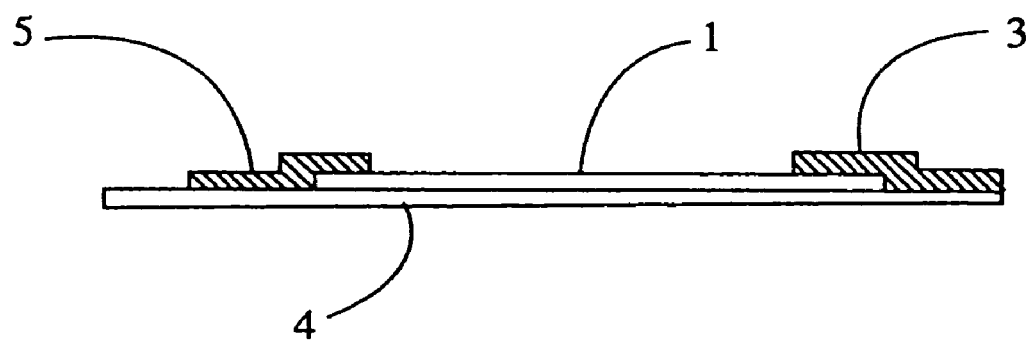

Another embodiment of the test strip for use in the practice of the present invention is shown in FIGS. 2A and 2B. In this embodiment of the invention, there is provided a reagent pad 5 at one end and absorbent pad 3 at the respective other end. In this regard, the reagent pad 5 is shown partially overlapping the test membrane 1 to thus produce a greater degree of saturation thereacross, as may be desired for a given application.

In either of the test strip embodiments depicted in FIGS. 1a-1c and FIGS. 2a-2b, it will be readily understood and appreciated by those skilled in the art that the same are designed to produce a lateral flow or path of migration that extends from the reagent pad 5 to the absorbent pad 3 at the other end. As per conventional test strip assays, the lateral flow of a reaction mixture across the test membrane 1 provides a basis for conducting chemical analyses over a given surface area (i.e., the test membrane 1).

Unlike prior art test strip assays, however, the assays and methods of the present invention do not utilize a capture barrier formed by bound receptors formed along a portion of the test membrane 1, but rather utilize a novel magnetic approach to generate such capture lines. In this regard, due to the novel methods and systems by which capture lines are generated via the present invention, it will be recognized that although the test strip configurations depicted in FIGS. 1 and 2 may be readily utilized in the practice of the present invention, the only essential element thereof comprises a chromatographic medium, such as a test strip or chromatographic plate, upon which a test sample may flow laterally thereacross. Accordingly, it will be understood that a path of migration need not necessarily be formed, as per conventional test strips and the like, in order to practice the present invention.

Test Membrane

The test membrane 1 can be selected from any available material having appropriate thickness, pore size, lateral flow rate, and color. It is preferred that the test membrane be made from a material which has a low affinity for the analyte and test reagents. This is to minimize or avoid pretreatment of the test membrane to prevent non-specific binding of analyte and/or reagent. Polyester is an example of a suitable test membrane material.

Reagent Pad

The (optional) reagent pad 5 can contain all or a portion of the reagents necessary to complete the assay. Reagents can include a capture ligand and reporter ligand which specifically bind different regions of the analyte to be detected in a given sample. The capture ligand can be covalently bound or absorbed to the surface of magnetic particles. Capture ligands can also be bound indirectly using binding partners such as anti-IgG antibody, streptavidin/biotin, and others. The reporter ligand is covalently bound to a dye, particle, radioisotope, or enzyme which produces fluorescence or luminescence. The reagent pad 5 can also contain stabilizers, buffers, surfactants and other agents which improve the performance of the assay. The reagent pad 5 receives the sample and all subsequent liquid reagents used to perform the assay. The reagent pad 5 also can be selected from any available material having appropriate thickness, pore size, and flow rate. It is preferred that the reagent pad be made from a material which has a low affinity for the analyte and test reagents. Again, this is to minimize or avoid pretreatment of the reagent pad 5 to prevent non-specific binding of analyte and/or reagent. Polyester and porous polyethylene are examples of suitable reagent pad 5 materials. The reagent pad 5 should be of sufficient size and void volume to accept the entire sample volume.

In some embodiments of the invention the reagent pad 5 may not be a physically separate component. Rather, instead the reagents can be stored in a reagent zone 2 formed on the test membrane 1 itself. In other embodiments of the invention, the reagent pad 5 does not contain reagents and instead is used as a liquid reagent receiving pad. As will be appreciated by those skilled in the art, by forming such reagent zones upon the test membrane as a substitute for reagent pads, the cost and complexity of manufacturing is substantially reduced insofar as the reagent pad component may be eliminated altogether. In this regard, the non-binding properties of the test membrane, coupled with the ability to form a capture line magnetically, as discussed more fully below, eliminates the need to design a test strip whereby a fluid sample must necessarily flow sequentially in one direction so that a given fluid sample with reagents thoroughly and precisely comes into contact with a conventional capture zone defined by a multiplicity of bound antibodies.

Absorbent Pad

The (optional) absorbent pad 3 should have absorbent capacity sufficient to contain all liquid volumes used during the test procedure. Cotton fiber and absorbent paper are examples of suitable absorbent pad 3 materials. As discussed above, however, the absorbent pad is optional insofar as the chromatographic medium utilized in the practice of the present invention may merely consist of a test membrane or chromatographic plate and does not necessarily require the use of an absorbent pad to produce or generate a direction of flow or path of migration for a given test sample, as is typically required in prior art assay strips.

Backing

The magnetic chromatography test strip backing 4 can be made of plastic, glass or other suitably rigid material. The backing length can exceed the length required to support the test membrane and pads, as may be desired to serve several functions. For example, such extended backing length can provide a handle or it can display information such as bar codes, fluorescent marks, and colored marks which can aid in the calibration of the individual test strip and multimode photometer, as discussed more fully below.

Figure 5A:
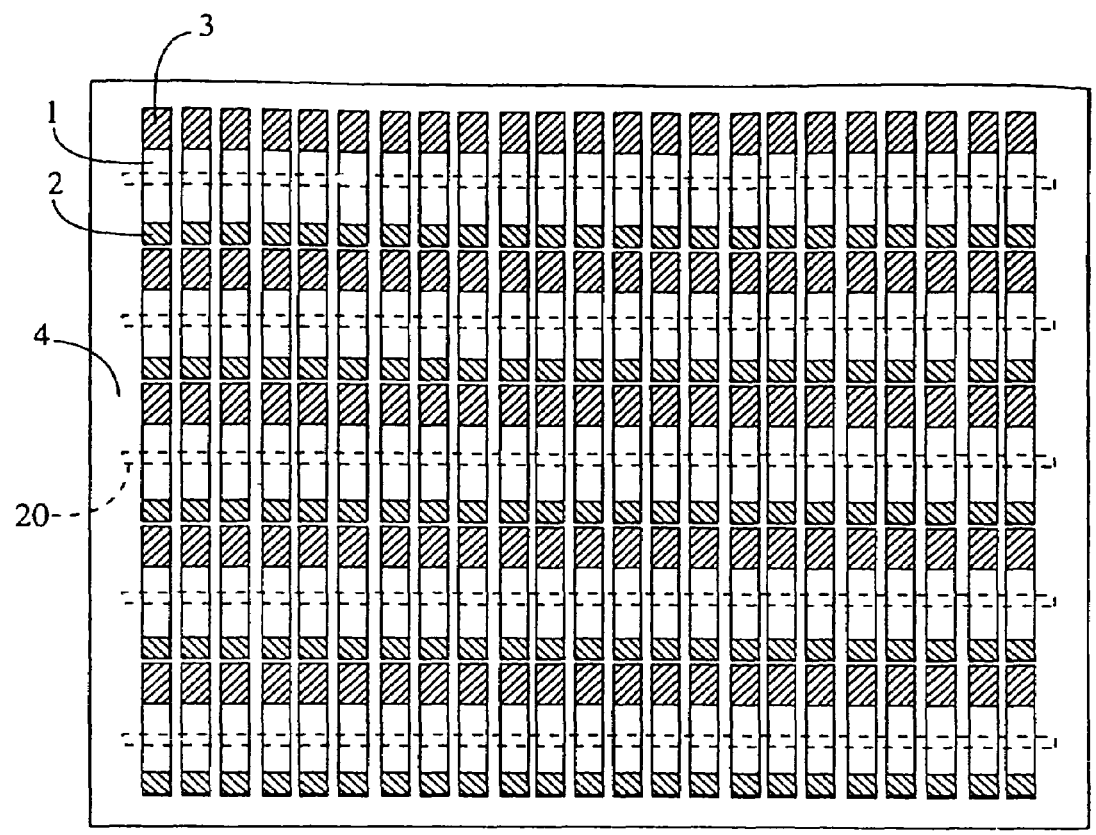
FIG. 5a is a top view of a multiplicity of test strips arrayed in parallel rows on a common backing for use in detecting the presence and quantity of one or more analytes from a plurality of samples.
Figure 5B:
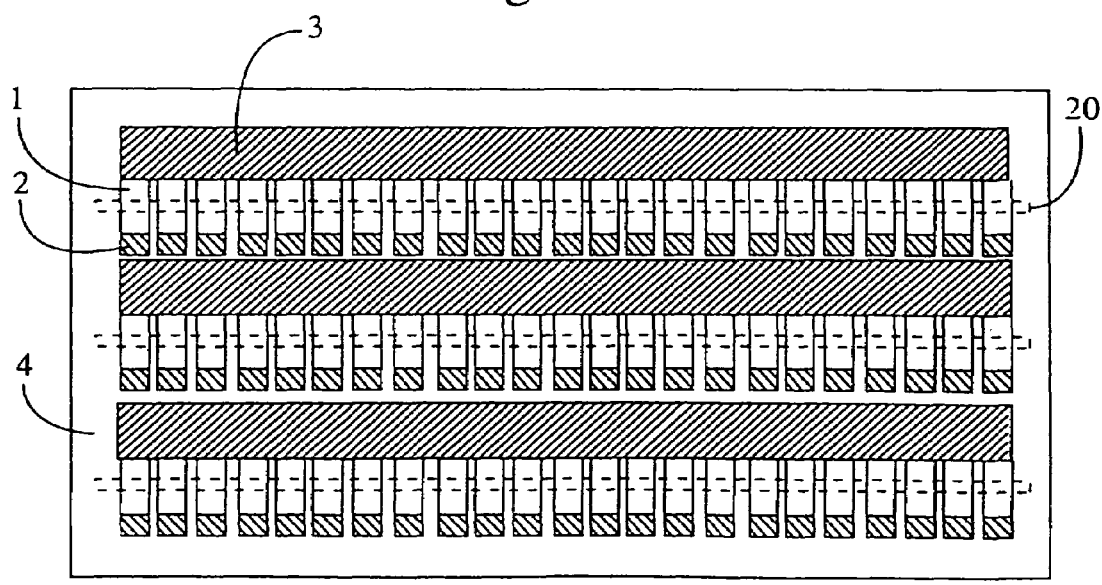
FIG. 5b is a top view of a multiplicity of test strips utilizing a single-common absorbent pad having fluid contact with a multiplicity of test membranes, the latter being arranged in a generally linear fashion.

In order to analyze a multiplicity of samples in a single analysis, there is further disclosed herein certain novel assay strips for performing such function. Referring now to FIG. 5a, there is shown a top view of a multiplicity of test strips arrayed in parallel rows on a common backing 4. The backing 4 has a top side and bottom side and can be in sheet or roll form and is preferably manufactured from an opaque plastic sheet material of appropriate color, thickness, and rigidity. Each respective test membrane 1 is sufficiently spaced to avoid fluid contact between adjoining test membranes 1. An absorbent pad 3 is preferably positioned to be in fluid contact at one end of the test membrane 1. FIG. 5b shows a top view of test strips manufactured using a single common absorbent pad 3 having fluid contact with all test membranes in a given row. Placement of test membranes 1 and absorbent pads 3 are such that multiple parallel rows of test strips are advantageously manufactured on a sheet or continuous web of backing 4. Each row of test strips is positioned with adequate spacing such that individual test strips for different rows are not in fluid contact with each other.

In order to identify the presence of a particular analyte, control, calibrator, or combination thereof, these novel methods of the present invention deploy a magnetic field at a specific site upon the test membrane portion of the test strips of the present invention. Such magnetic field, which may be generated by any type of magnetic source, such as a permanent magnet or an electromagnet, is selectively positioned such that when applied to a portion of the test membrane, magnetic particles present within a given sample that are flowing laterally across the test membrane will become substantially bound at the specific site where the magnetic field is applied. In this regard, the applied magnetic field attracts the magnetic particles forming a magnetic barrier that selectively retains magnetic particles, with the analyte of interest having complexed thereon with appropriate labels bound thereto, while allowing the remainder of the reaction mixture to continue the flow laterally across such barrier or zone. With respect to those strips depicted in FIGS. 5a and 5b, to generate the desired capture zones of lines, a magnetic barrier is formed using a bar magnet(s) 20 laminated or placed in close proximity to the bottom side of backing 4. The bar magnet(s) or magnetized rail(s) 20 is positioned perpendicular to the test membrane(s) 1 in each row and between said test membrane (s) 1 fluid receiving and absorbent ends. A reagent zone 2 is positioned at the fluid receiving end of each test membrane.

By selectively applying the magnetic field about or upon the test strip, a capture line is magnetically assembled thereon insofar as magnetic particles are substantially immobilized by the magnetic field at a specific site of sites situated across the test membrane. The remaining reaction mixture components which are not magnetically bound thus continue to flow laterally within the test membrane, typically in a path of migration toward an absorbent pad. Advantageously, such method allows more than one analyte, control, calibrant, or combination of these to be quantitatively assayed on a single test strip. Accordingly, it is an object of this invention to provide a useful method for the performance of assays, e.g. biological assays.

While the test strips depicted in FIGS. 1a-1c and FIGS. 2a-2b depict only one section of test membrane disposed between a reagent pad and an absorbent pad, it will be recognized by those skilled in the art that when more than one analyte, control, calibrator, or combination thereof are to be assayed within a test solution using a single test strip, a cascade of reagent zones or pads can be placed down stream from the first applied magnetic field. Several schematic examples of flow test strip assemblies which can be used with magnetic chromatography are given:

Single Assay
reagent zone 1/test membrane//absorbent pad
reagent pad 1//test membrane//absorbent pad
Multiple Assay
reagent zone 1/test membrane/reagent zone 2/test membrane//absorbent pad
reagent pad 1//test membrane//reagent pad 2//test membrane//absorbent pad
Opposing Multiple Assay
reagent zone 1/test membrane//absorbent pad//test membrane/reagent zone 2
reagent pad 1//test membrane//absorbent pad//test membrane//reagent pad 2
where:
symbol/designates a phase boundary within a single chromatographic medium; and
symbol//designates a union of two separate mediums (chromatographic and other).

As a consequence, the multiple assay examples given causes test solution to encounter two groups of magnetic particles. The flow of test solution is unilateral moving from reagent zone or pad 1 at one end of the test strip to absorbent pad at the opposite end of the test strip. Magnetic barriers are positioned at each test membrane. The first magnetic barrier is positioned across the test membrane prior to reagent zone or pad 2 while the second magnetic barrier is positioned across the test membrane prior to the absorbent pad. Reagents from reagent zone or pad 2 can be used to analyze additional analytes in the test solution or can be used to perform calibration or quality control.

The opposing multiple assay example given will allow assay of identical analytes from separate test solutions. This is advantageous when a calibrator must be assayed simultaneously with a test sample. The flow of test solution is from each reagent pad or zone toward a single common absorbent pad. Magnetic barriers are positioned across each test membrane. It is also anticipated by the invention that magnetic chromatography can be used with other multiple assay test strip configurations including rosettes, parallel arrays, and others.

In order to manipulate the width (i.e., surface area) of the capture line formed by the application of a magnetic field to the test strip, it has been unexpectedly discovered that the width of such capture line may be selectively controlled depending upon the number of magnets and/or degree of magnetic force applied to the test membrane. In this regard, it has been discovered that by stacking multiple magnets upon one another beneath the test membrane where the captures zone is sought to be formed, the increased number of magnets applied thereto correspondingly produces an increase in the width of the capture line. As will be appreciated by those skilled in the art, by utilizing a greater degree of magnetic force, the corresponding capture line produced thereby will have a greater surface area which, as a consequence, can be utilized to determine concentration per unit area. Along these lines, it is contemplated that manipulating the magnetic field to produce a wider or narrower capture line or area may prove extremely beneficial. For example, by manipulating the width or surface area of the capture line, a means may thus be provided to facilitate the inspection of individual particles utilizing a microscope. Likewise, such selective manipulation of the capture zone may be used to isolate target cells from a population of cells, and thereafter perform microscopic inspection thereof as may be necessary for a given application.

With respect to the dimensions of such magnets that are preferably utilized in the practice of the present invention, it is currently believed that bar magnets and/or magnetized rails may be utilized whose width is between 0.003 to 3.0 inches, and whose length is between 0.010 inches to 100 inches. In this regard, it will be understood that such magnets, and in particular magnetized rails, may be sized and configured to generate any degree of magnetic field necessary to form a desired capture line and may be readily determined for a given application by one having ordinary skill in the art.

Figure 6A:
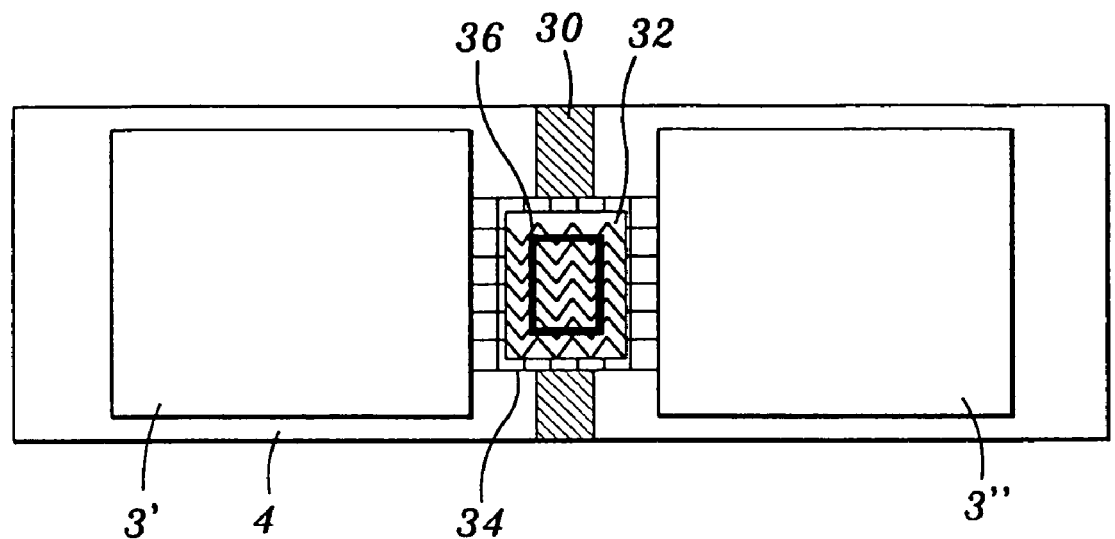
FIG. 6a is a top view of an assay test strip constructed in accordance with a third preferred embodiment of the present invention.
Figure 6B:
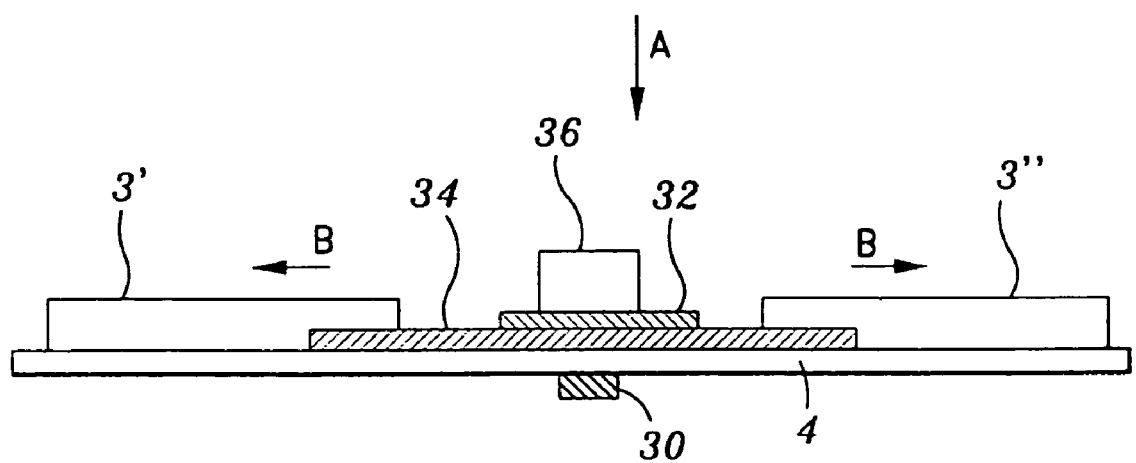

Referring now to FIGS. 6a and 6b, there is shown a third embodiment of a test strip for performing the assays of the present invention. Unlike the aforementioned embodiments, however, such test strip is specifically designed and configured to form a capture line at the point of contact at which a reaction mixture containing magnetic particles is introduced to the strip. In this regard, and in contrast to the other aforementioned embodiments, the test strip according to the embodiment depicted in FIGS. 6a and 6b does not require the reaction mixture to flow according to a unilateral pathway extending from the absorbent pad, across the test membrane, and ultimately over the magnetic field by which the capture line is ultimately created.

As will be recognized by those skilled in the art, by forming the capture point at the initial point of contact at which the reaction mixture is contacted with the test strip, there is advantageously conserved the amount of analyte sought to be detected through the assay which, unlike prior art devices and methods, can diffuse away from the capture zone of bound receptors or otherwise be restrained from reaching such capture zone due to nonspecific binding. As is well-recognized in the art, a significant portion of the analyte sought to be detected through use of conventional assays can go undetected by virtue of the sequential lateral flow that must occur from when the reaction mixture is introduced to an assay to the point where such reaction mixture comes into contact with the bound receptors forming the sought-after capture line.

Referring initially to 6a, such embodiment comprises an elongate backing 4 having first and second opposed ends and an intermediate portion. As stated above, such backing may be made of glass, plastic, or other suitably rigid material. Formed upon the opposed ends of the backing are first and second absorbent pads 3', 3" which, as discussed more fully below, caused the reaction mixture to ultimately flow bilaterally from the point of contact at which the reaction mixture is introduced to the test strip. Affixed underneath the backing 4 is an elongate magnet 30, which is utilized to create the capture line for use in further analysis. In the alternative, the elongate magnet 30 may be proximately positioned underneath the backing 4 in order to yield a plurality of advantages, such as facilitating microscopic applications.

Formed upon the intermediate portion of the backing 4 between the first and second absorbent pads 3', 3", and centered over the magnet 30 are preferably provided first vertical flow mesh 32 and second lateral flow mesh 34. As illustrated, the vertical flow mesh 32 is formed on top of lateral flow mesh 34, the latter being in contact with the first and second absorbent pads 3', 3" on opposed sides thereof. Preferably, a portion of the lateral flow mesh 34 is partially positioned underneath the first and second absorbent pads 3', 3" as shown. In order to introduce the reaction mixture, there is further preferably provided a sample well 36 which is specifically designed and configured to introduce the reaction mixture directly upon the first vertical mesh 32 so that the same thereafter sequentially flows to the lateral flow mesh 34 and ultimately to the absorbent pads 3', 3" via bilateral flow.

According to a preferred embodiment, the vertical flow mesh 32 is formed of polyester, nylon, glass fiber or any other like material and is oriented to facilitate downward flow therethrough in order to filter large debris which may be present in the test solution. The lateral flow mesh 34 is similarly formed from polyester, nylon, glass fiber or any other like material to allow bilateral flow to the respective absorbent pads 3', 3". The lateral flow mesh 34 may also be formed from materials having magnetic properties, such as metal screens, metalized polyester and the like. The sample well 36 is preferably formed from a non-magnetic material such as plastic, and in particular polyvinyl chloride, so as to not react with the magnetic particles present within the reaction mixture.

As an alternative to providing an arrangement of meshes, such as the combination of first mesh 32 and second mesh 34, discussed above, it is contemplated that the backing 4, and more particularly the intermediate portion thereof may be formed to have a texturized surface that is configured and oriented to direct the flow of sample flowing thereacross. In this respect, it is contemplated that any textured surface capable of causing lateral flow of the test solution across the intermediate portion of backing 4 may be utilized in the practice of the present invention, and in particular as a substitute for the lateral flow mesh 34.

Referring now to FIG. 6b, there is shown the sequence by which an assay may be performed using the embodiment depicted in FIG. 6a. Initially, the reaction mixture is deposited within the sample well 36. Due to both capillary action and downward gravitational forces, indicated by the letter A, the reaction mixture is sequentially caused to pass through vertical flow mesh 32, lateral flow mesh 34 and ultimately to absorbent pads 3', 3" via lateral flow depicted by the letter B. However, the magnetic particles having the analyte of interest complexed therewith will be caused to become substantially bound within the magnetic zone defined by magnet 30 disposed underneath the backing 4. As such, the magnetic particles become captured at the starting point of the assay, as opposed to at some point removed from where the reaction mixture is initially introduced, as occurs through most conventional strip assays. In the alternative, the use of textured surfaces formed directly on back 4, or attached thereon, may be contemplated. More specifically, any textured surfaces capable of causing lateral flow of the test solution can be utilized as a substitute for the lateral flow mesh 34.

Advantageously, the analyte sought to be detected is conserved and is not allowed to diffuse or otherwise become bound outside the capture line. As such, such embodiment provides enhanced sensitivity that has not heretofor been before available. Along these lines, it is contemplated that the embodiment depicted in FIGS. 6a and 6b are exceptionally advantageous for use in isolating particular types of cells, such as cancer cells, and other large molecules and biological structures. In this respect, because of the size of such structures, coupled with their limited quantities in a given sample (e.g. one cancer cell in fifty billion cells, as can be found in a 10 ml blood sample), such structures have been difficult to isolate and detect in the past. In this regard, due to their size, such structures are physically prevented from reaching the capture or target sites provided to detect their presence. In such applications, it is found that the nylon mesh, as utilized for the lateral flow mesh 34, is exceptionally advantageous insofar as the same has been shown to substantially increase lateral flow velocity of the reaction mixture away from the capture zone (i.e., the magnetic field generated by magnet 30), which thus increases non-target cell wash out. As a result, target cells may be retained in greater concentrations and hence may be more easily detected than prior art techniques.

Figure 7A:
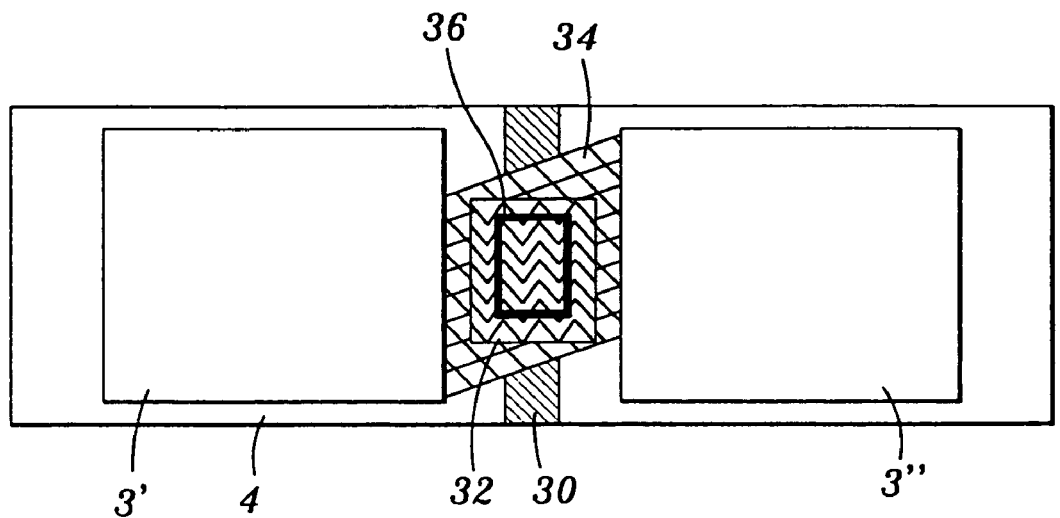
FIG. 7a is a top view of an assay test strip constructed in accordance with a fourth preferred embodiment of the present invention.
Figure 7B:
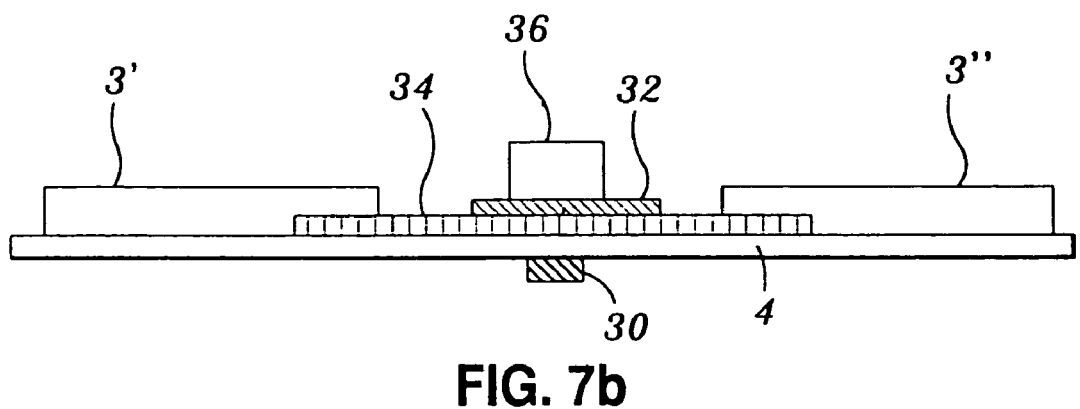

To further enhance the ability of the test strip embodiment depicted in FIGS. 6a and 6b to increase cell wash out (i.e., facilitate separation and isolation of the target cells from a reaction mixture), there is provided an alternative bilateral flow test strip depicted in FIGS. 7a and 7b. Referring initially to 7a, there is shown the same components of the test strip depicted in FIGS. 6a and 6b. Specifically, there is provided a backing 4 with first and second absorbent pads 3', 3" formed upon the opposed ends thereof. Disposed underneath the backing 4 is magnet 30, provided to generate the magnetic field necessary to produce the desire capture line. There is further provided a sample well 36 for introducing the reaction mixture to the test strip, followed by vertical flow mesh 32 and lateral flow mesh 34.

With respect to the latter, however, such lateral flow mesh 34 is designed to have a generally diagonal orientation relative the vertical flow mesh 32. As will be appreciated by those skilled in the art, by providing a diagonal orientation of the lateral flow mesh 34 relative the vertical flow mesh 32, the reaction mixture flowing therethrough experiences increased velocity in flowing to the opposed absorbent pads 3', 3". In this regard, the reaction mixture avoids having to flow in a perpendicular direction per the embodiment depicted in FIGS. 6a and 6b, and, as such, does not experience the degree of impedance as would a reaction mixture encounter via the embodiment depicted in FIGS. 6a and 6b. As discussed above, as an alternative to utilizing a diagonally oriented lateral flow mesh 34, the intermediate may be to have a texturized surface that is operative to define a specified pathway and flow velocity of the sample flowing thereacross.

Figure 8:
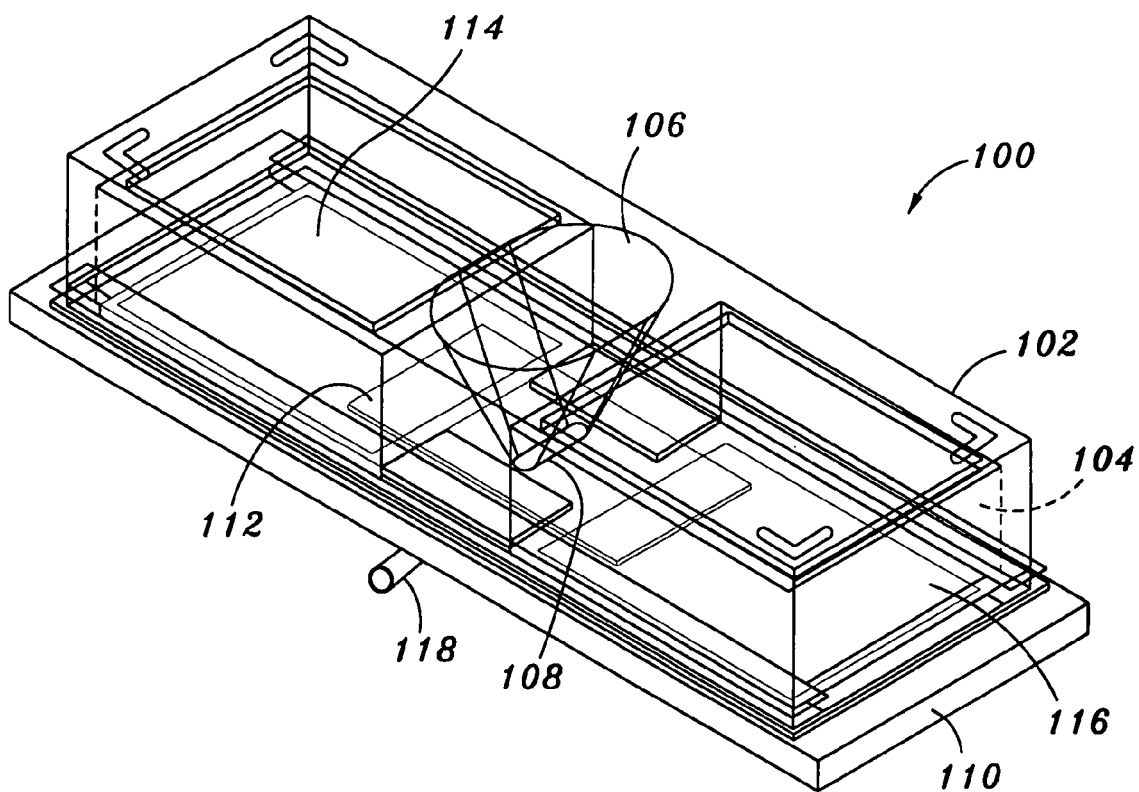
FIG. 8 is an elevated perspective transparent view of a multi-conformable assay system constructed in accordance with a preferred embodiment of the present invention.
Figure 9:
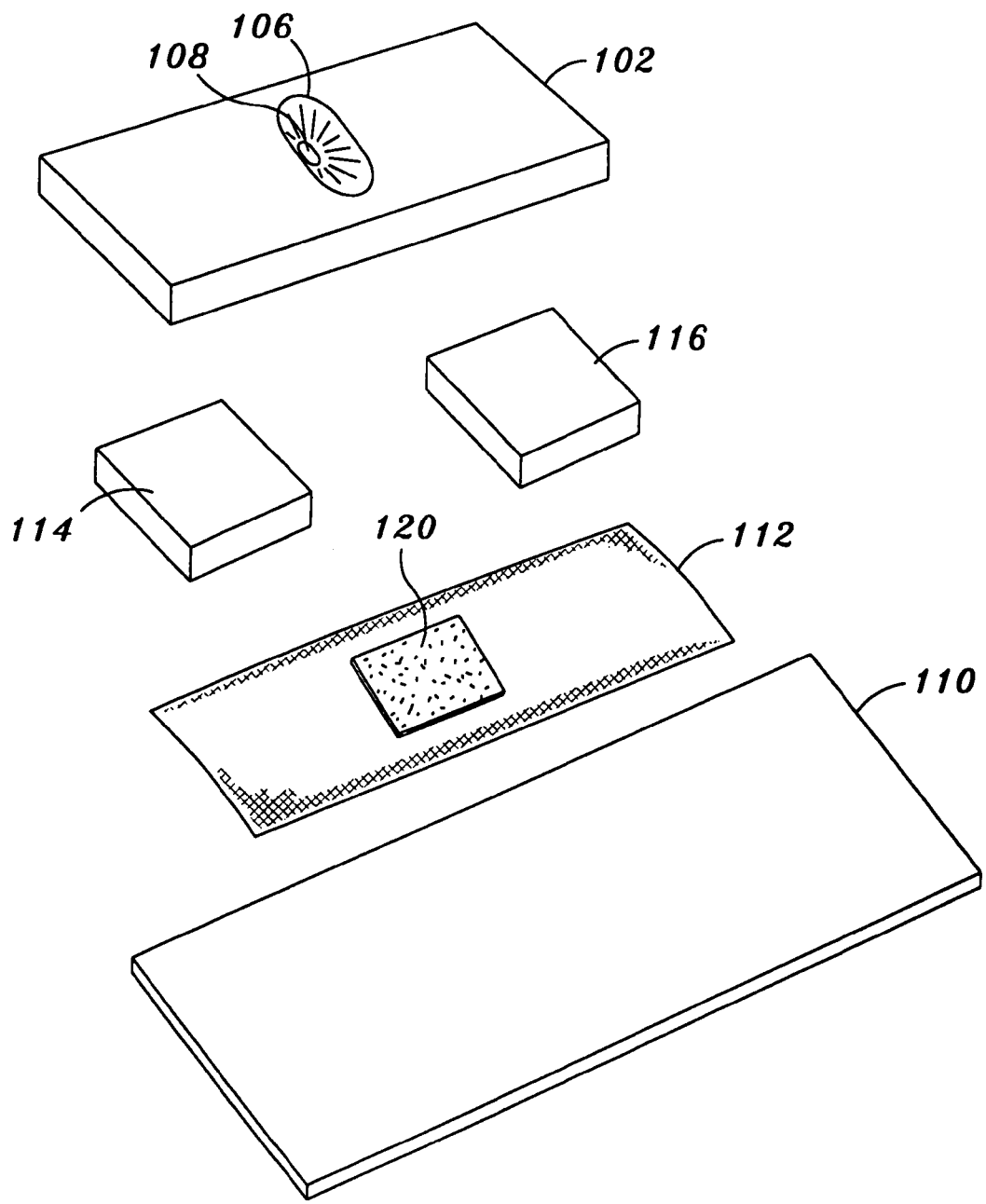
FIG. 9 is an exploded view of an assay constructed in accordance with the principles of the assay depicted in FIG. 8.
Figure 10:
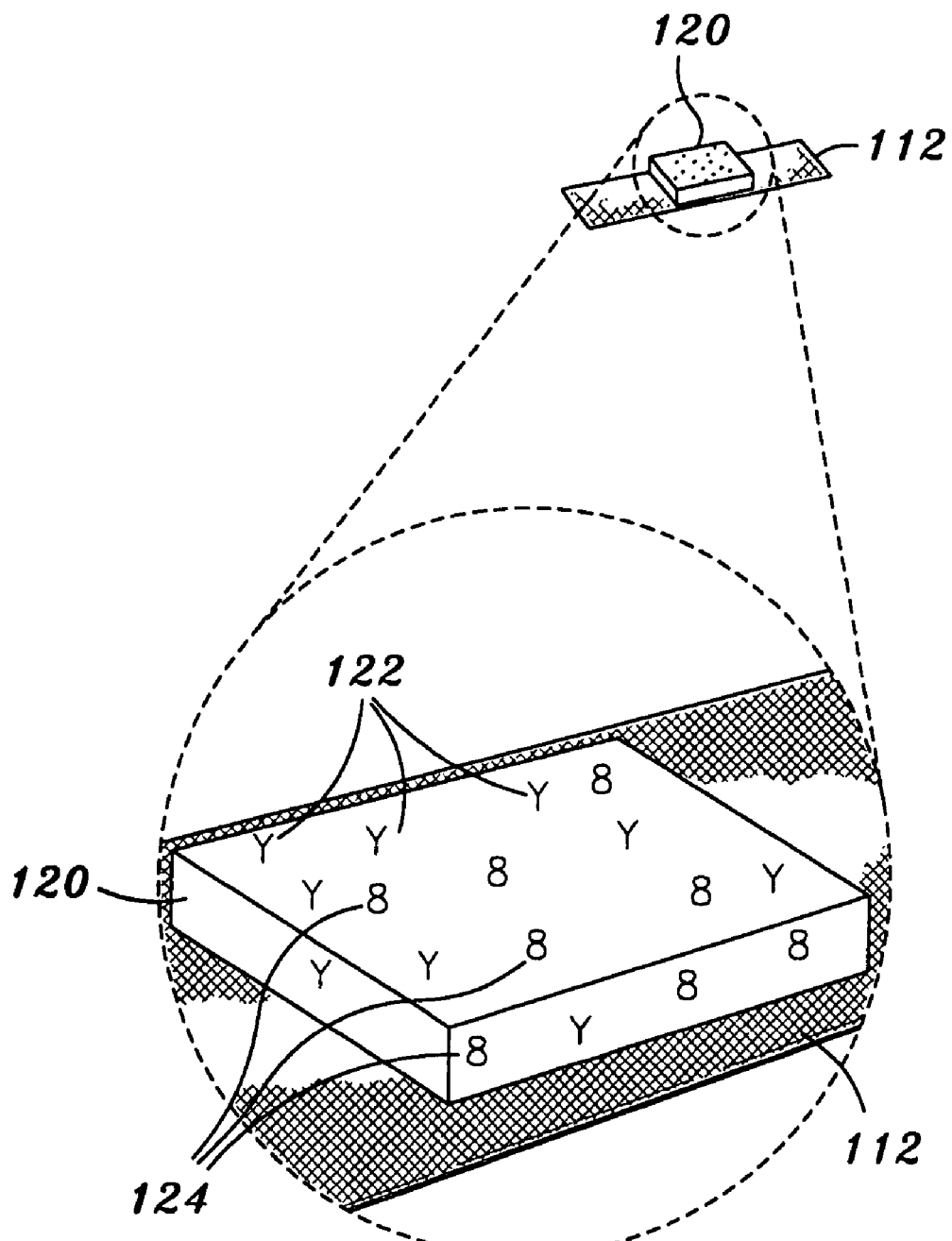
FIG. 10 is an expanded view of a gel layer deposited upon the mesh of the assay depicted in FIG. 9 for use in facilitating the capture, isolation and further biochemical processing of a target analyte present therewith.

Referring now to FIGS. 8-10, and initially to FIG. 8, there is shown an assay system 100 that is multi-configurable in nature and thus enables the same to be used in a wide variety of applications that has not heretofore been available. In this regard, the assay system 100, by relying on the aforementioned principles and structure, can be selectively fashioned to not only accomplish the aforementioned objectives of providing greater capture and isolation and conservation of fluid specimens, but also provide a simple, rapid, reliable system that permits the efficient handling of small or large numbers of specimens. Likewise, such assay system 100 is exceptionally effective in performing assays related to cell isolation, sorting and interrogation, as discussed more fully below.

As depicted, the system 100 comprises a housing 102 that defines an interior chamber 104. The housing 102, which is preferably formed from any suitable rigid material such as plastic and/or metal and have a black color to minimize photo degradation of potentially-sensitive proteins, cells and other cellular components, will be configured to and mounted upon base 110. As discussed more fully below, the housing 102 may be configured to either be permanently affixed to base 110 or formed to be detachably fastenable therefrom, typically by either mechanical and/or adhesive means.

Formed upon the center of housing 102 is sample well 106, which as illustrated has a generally frusto-conical configuration that tapers to define an opening 108. As will be recognized by those skilled in the art, the sample well 106 provides means for depositing a reaction mixture suspected of containing an analyte of interest that will ultimately be captured and isolated as discussed above. To that end, the sample well 106 with opening 108 defined thereby will deposit a reaction mixture upon a target area that may optionally be defined by layer of mesh 112, the latter being desired to rest upon base 110 and, optionally, become sandwiched between housing 102 and base 110. To facilitate the bilateral flow of the reaction mixture, the interior 104 of housing 102 will define spaces for absorbent members, which may be materials such as wicks or pads 114, 116 as shown that are disposed on opposed sides of the sample well 106. As discussed above, pads 114, 116 will be operative to draw away that portion of the reaction mixture, via lateral flow, that does not contain the magnetic particles that will have complexed with the analyte of interest. With respect to the latter, the same will be retained at the point of deposition upon the target area by virtue of its contact with the magnetic field generated by magnet 118. As discussed above, the magnetic field may be generated by a variety of means known in the art and may be either integrated as part of base 110, detachably fastenable to base 110, or completely detached therefrom. Along these lines, it is contemplated that the target area upon which the analyte of interest is captured will be approximately 0.6 cm$^2$ compared with 4 cm$^2$ of inspection area as per conventional cover slips.

Referring now to FIG. 9, there is shown an exploded view of an assay constructed in accordance with the assay system 100 of FIG. 7 that, for reasons that will be discussed, can be selectively constructed to perform an enhanced assay function. As illustrated, in its most basic components the assay will comprise housing 102 having sample well 106 and aperture 108 formed thereupon. Absorbent pads 114, 116, disposed on opposed sides of the sample well 106 and confined within the interior of housing 102, are provided to draw out a portion of the reaction mixture not containing the magnetic particles complexed with the analyte of interest. As further illustrated, a mesh 112 may be provided upon which absorbent pads 114, 116 will rest upon such that the reaction mixture will flow bilaterally thereacross. Disposed on the center of the mesh 112 is capture area 120 that is aligned to be directly beneath opening 108 so that the sample that is deployed through the assay will be conserved and captured at discreet area of isolation. Capture area 120, as discussed more fully below, may take a variety of forms, and may include a second layer of mesh or, as discussed more fully in connection with FIG. 10, may comprise a novel receiving gel that may provide an enhanced capture mechanism that may be configured to form a variety of biochemical functions.

Base 110 is further provided and serves not only as a structural support for the other assay components, but may also be useful in performing further processing related to the assay. Along these lines, it is contemplated that base 110 may take the form of a conventional, standard microscope slide. Moreover, in those applications where the base 100 is utilized as a structure for capturing cells, the same may be utilized to initiate the formation of a cell culture. As will be recognized by those skilled in the art, the identification, isolation and eventual growth of a cell culture via a one step assay process has not heretofore been available, and much less as efficient and effective as those of the present invention at not only being able to detect and isolate exceedingly small quantities of cells that may be present in a sample, but thereafter directly grow such cells to generate a cell culture.

Given the foregoing description of the components of the assay system 100 discussed in relation to FIGS. 8 and 9, there is now provided a discussion as to how the various components can be selectively chosen and interconnected to perform specific types of assays having an enhanced function for performing a given assay procedure.

In the embodiment depicted, the assay system 100 is operable and readily scalable from single slide bench top applications to a continuous high throughput screening environment. Specifically, the assay can be used for a single slide bench top applications, small batch testing, automated batch processing and continuous high throughput screening (HTS). In such applications, the base 110 may take the form of a standard microscope slide, which easily adapts to existing fluid handling systems, such as Gilson and Tecan Systems. In this regard, such systems allow for large batch processing and walk-way automation, and eliminate the need for massive robotic transfer systems and other expensive capital equipment.

For procedures involving cell isolation, sorting and interrogation, the assay system 100 can be selectively modified to suit a particular application. In applications involving cell engineering and interrogation, the basic assay system depicted in FIGS. 8 and 9 will be preferably formed from all non-detachable parts comprised of housing 102, absorbent pads 114, 116, mesh 112 and base 110, the latter preferably taking the form of a microscope slide. In such configuration, the assay will preferably be able to handle samples of 4-8 ml. and further allow for serial additions of reagents for immunofluorescent analysis. Analysis of staining can be performed either manually or digitally using an inverted microscope usually at 40×.

For cell engineering and expansion applications, the assay can be modified such that the housing 102 and absorbent pads 114, 116 will be selectively removable to thus leave mesh 112 in place. Such configuration allows for simple culture methods and post-purification of target cells (e.g., transfection, drug resistance, etc.). Such configuration also provides a platform for post-culture analysis such as immunofluorescence, FISH, etc. analysis of culture staining can be performed either manually or digitally using an inverted microscope, usually at 40×.

For applications involving cell resistance and interrogation, the assay system 100 may be configured such that the housing, absorbent pads 114, 116 and mesh 112 are removable from base 110. In such applications, a target area (not shown) will be defined directly upon base 110, upon which the purified product will be left naked. Such an assay will be ideal for placing cells in altered medium, such as Matrigel, for drug resistance testing. Moreover, such configuration may further provide ideal for FISH testing. To that end, the assay according to such construction may preferably support flexible microscope evaluation using either inverted or conventional, manual or digital equipment (from 10×-100×).

For applications involving cell sorting and serial interrogation, the assay can be configured such that the housing 102 is removable. As a result, base 110 is left with the absorbent pads 114, 116 remaining attached thereto. The mesh 112 may be selectively fashioned and configured to be either left on site upon base 110, or selectively removed therefrom. Such configuration permits serial additions of reagents for assays such as FISH, immunofluorescence, and cell-based PCR.

In yet a further refinement depicted in FIG. 10, it is contemplated that the target area may be defined by a gel 120 that is operative to facilitate the capture, isolation and possible further biochemical processing of the target analyte captured thereat. Such gel, which can comprise any of a variety of biocompatible gels well-known to those in the art, such as polyacrylamide gels utilized in electrophoresis and the like, may serve as a medium for capturing and isolating cells, intracellular structures, proteins, genes, and the like. Such gel 120 may be either formed on a mesh backing 112 as shown, or otherwise formed directly on base 110. Other substrates (not shown) may also be utilized to support gel 120 at or around the target area. To enhance the capability of the gel 120 to capture and isolate cells, intracellular structures, etc., it is contemplated that such gel may be provided with receptors 122 specific for the target analyte of interest. In this regard, by suspending such receptors 122 or, alternatively, having the receptors 122 bound to a solid phase, can facilitate the ability of the assays of the present invention to provide enhanced capture and isolation of target analytes.

In addition to or separate from such receptors 122, the gel, as depicted as 120 in FIG. 10, may be provided with other chemical modifiers, reagents or enzymes, depicted as 124, that may be operative to provide further biochemical processing of the analyte of interest. One contemplated application includes the use of digestive enzymes to selectively cleave proteins or otherwise digest target intercellular components for further isolation and identification. To that end, it is contemplated that formulation and composition of such gel compositions having the desired reagents, receptors, enzymes, and the like will be readily known and capable of being made by those skilled in the art using known techniques. In a further contemplated application, the gel 120 may serve as a growth medium for cells to thus enable a target cell of interest to be expanded or propagated to thus create the formation of a cell culture. To attain such objective, it is contemplated that a variety of nutrients and other growth media well-known to those skilled in the art may be incorporated as part of gel 120.

Advantageously, the assays of the present invention offer greater flexibility than microtiter plates and can be efficiently used for cellular sub-population analytic assays while simultaneously determining the presence of aberrant DNA, mRNA transcription expression, and protein translation expression (simultaneous FISH/IF). The assays of the present invention can likewise be used to isolate and sort cells, proteins or genes with one self-contained unit, thereby eliminating the need for separation columns. Moreover, by virtue of the direct addition of sample, reagents, and cell wash solutions through the well 106 eliminates cell transfer steps, really expedites the assay procedure, enhances cell capture, lowers cell loss, and minimizes the chance of error. Along these lines, it is further contemplated that the assays of the present invention can be specifically configured such that the interconnection between housing 102 and base 110 will define one or more openings that will define a channel through which further post-assay assessment and manipulation can be conducted. For example, it is contemplated that the interconnection between base 102 and 110, whether or not such structures are permanently affixed or detachable from one another, such elements 102, 110 may cooperate to define one or more channels through which cellular testing may be conducted or otherwise allow reagents to be introduced therethrough to facilitate cellular lysing/digestion and/or other reagents to facilitate separation and isolation of target proteins, organelles, and the like.

As will be appreciated by those skilled in the art, the assays of the present invention, by virtue of their multi-functional configurations may be used in a number of applications, particularly with respect for use in drug discovery. To that end, the assays of the present invention may be exceptionally effective to determine the effect of the compound on a cell for efficacy and potential toxicity. As is well-known, current techniques utilized to differentiate the expression profiles of pure cell populations, advanced separation techniques and novel gene expression methods are complex, costly, labor intensive, and not readily scalable. Not only do the assays of the present invention overcome such disadvantages of the prior art, the same actually have far more wide spread application. Along these lines, the assays of the present invention are exceptionally effective at forming both target identification and target validation procedures. With respect to the former, which include procedures such as cell isolation, organelle or sorting, and protein fractionation, and the latter, which can involve specific protein isolation, immune assays, and molecular analysis, often times required capture and isolation of cells, proteins or genes that remain functionally and structurally intact. At times, however, such targets are often fragile, membrane bound, or of exceptionally small or large size. Despite such difficult properties or characteristics, however the assays of the present invention are well-suited to facilitate the separation and isolation of such targets in a manner that is superior to that of the prior art.

The present invention further includes a novel analyzer having a multimode photometer module included therein which can measure front surface fluorescence (fluorimetry mode), luminescence (luminometry mode), and reflectance (densitometry mode) at a single focal point on a test strip. The use of multiple optical methods at a single focal point provides information regarding the quality and structure of an individual capture line as well as the amount of analyte, control, or calibrator present at the capture line. Thus an object of the invention is to minimize accuracy and precision problems associated with test strips by interrogating important test strip locations using two or more optical methods.

Figure 3B:
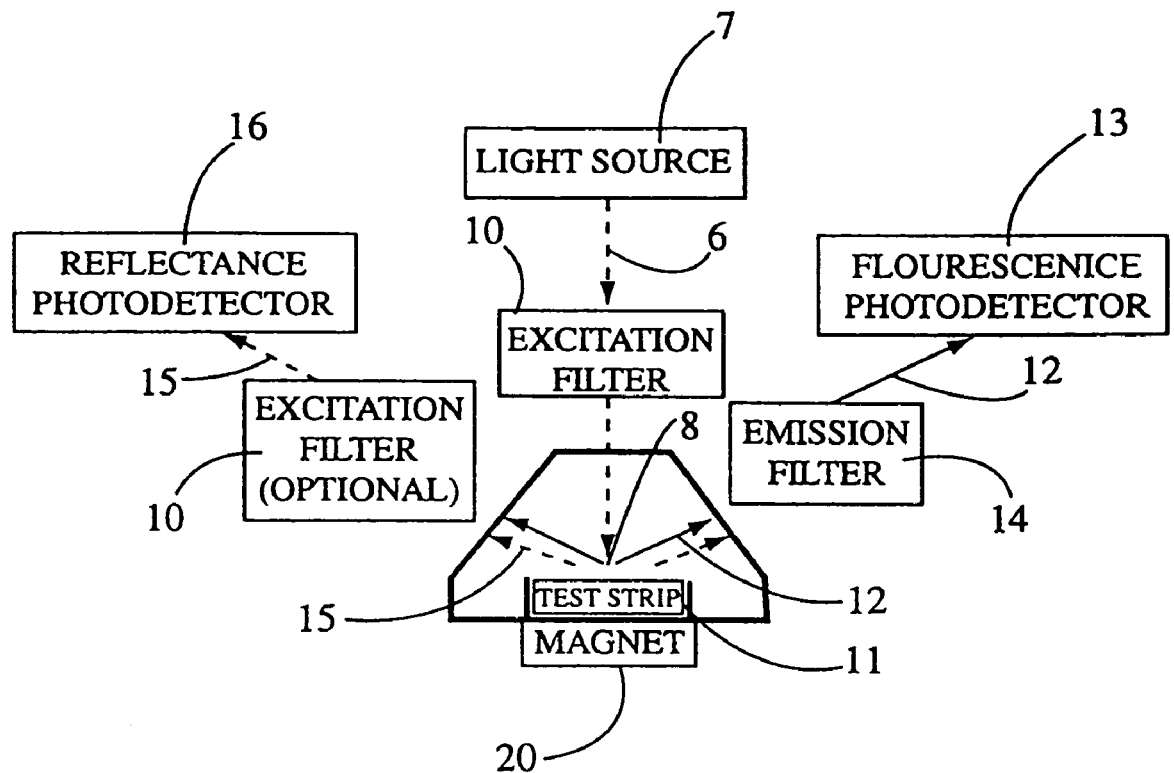
FIG. 3b is a cross-sectional view and block diagram of the multimode photometer depicted in FIG. 3.
Figure 3A:
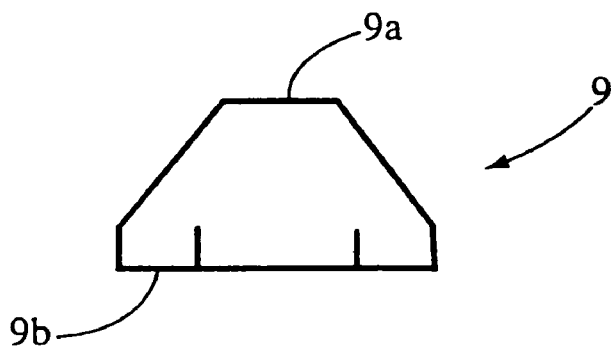
FIG. 3a is a cross-sectional view of a multimode photometer constructed in accordance with a preferred embodiment, as utilized in the practice of the methods of the present invention.

As illustrated in FIG. 3a, the multimode photometer consists of an optical canopy 9a and a base 9b which cooperate to form an optical tunnel 9. The optical tunnel 9 aligns light sources and photodetectors, with magnetic sources and test membranes, chromatographic plates, etc. to form optical paths. In this regard, base 9b includes a channel formed therein for receiving a test strip of the aforementioned variety. The base 9b further preferably includes a magnetic source fixed therein or fixed relative the channel to thus create the desired capture line at a specified location within the optical tunnel 9. For example, a magnetic source, such as a magnet, may be placed beneath the base of the optical tunnel 9b such that the test strip rests in the channel situated thereabove.

The optical canopy 9a is formed to have a ceiling through which a light source may be transmitted, and angled sidewalls through which the resultant reflected light may be emitted. As will be recognized by those skilled in the art, the multimode photometer, and more particularly the optical tunnel defined thereby, may be extruded, machined, or molded from any of a variety of suitable opaque materials, including but not limited to PVC, ABS, or anodized aluminum. As such, the optical tunnel 9 of the present invention may be fabricated inexpensively from inexpensive materials.

Referring now to FIG. 3b there is schematically illustrated the components utilized for analyzing a test strip with the multimode photometer of the present invention. Initially, an excitation path 6 is formed from the light source 7 to a focal point 8 at the base 9b of the optical tunnel 9. As will be readily appreciated, the magnetic source incorporated into the base 9b for forming the capture line on a given test membrane or chromatographic plate will be precisely aligned with the excitation path 6 such that the path 6 is directly aimed at the capture line produced by such magnetic source. As will be appreciated, light emitting diodes (LEDs), laser diodes, mercury vapor lamps, and xenon lamps are among many suitable light sources which can be used. If necessary, an optical filter 10 can be used to select an excitation wavelength 6. This excitation filter 10 can be placed on either side of the canopy wall 9a provided, however, the same is in the excitation path 6 between the light source and test strip 11. When a test strip 11 is inserted into the optical tunnel 9, such strip is held in position at the base and intersects the excitation path 6 at the focal point 8.

Emission paths 12 are formed from the focal point to one or more photodetectors 13. Apertures are positioned using a radial geometry in the canopy wall 9a at angles which optically align each photodetector 13 with the focal point 8. Light pipes, optical fibers, and other wave guides can be used to transmit emission light to the photodetectors 13. Excitation light 6 excites fluorophores present on the test strip 11 at the focal point 8, which then emit light 12 of a longer wavelength. If luminescence is used excitation light 6 is not required and can be omitted during luminescence measurement. Emission filters 14 are used to specifically select the emission wavelength 12 of the light emitted from the flourescent or luminescence and to remove traces of excitation light 6. As will be appreciated by those skilled in the art, such emission filter 14 can be placed on either side of the canopy wall 9a providing it is in the emission path 12 between the photodetector 13 and test strip 11.

Reflectance paths 15 are also formed from the focal point 8 to one or more photodetectors 16. Such reflectance path 15 carries both excitation 6 and emission light 12. If necessary, excitation filters 10 can be used to specifically select the excitation wavelength 6 of the light reflected from the test strip and to revoke traces of emission light 12. This excitation filter 10 can be placed on either side of the canopy wall 9a providing it is in the reflectance path 15 between the photodetector 16 and test strip 11.

The filters 10 and 14 can be of the type known in the art as interference filters, due to the way in which the same block out-of-band transmissions. In this respect, interference filters exhibit an extremely low transmission outside of their characteristic bandpass and, as such, are very efficient in selecting the desired excitation and emission wavelengths.

As will further be appreciated by those skilled in the art, an optical tunnel can have multiple focal points at which photometric measurements can be made simultaneously, which advantageously allows multiple points on a test strip to be used for sample analysis and/or calibration. In such applications, optical components, such as LEDs, photodiodes, and interference filters, may be clustered at each focal point along the optical tunnel.

Figure 4A:
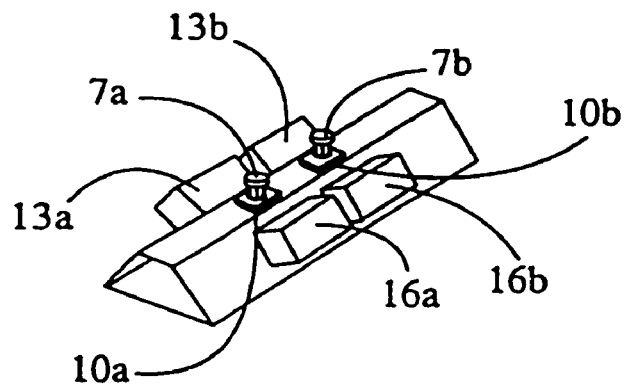
FIG. 4a is perspective view of the multimode photometer depicted in FIG. 3.
Figure 4B:
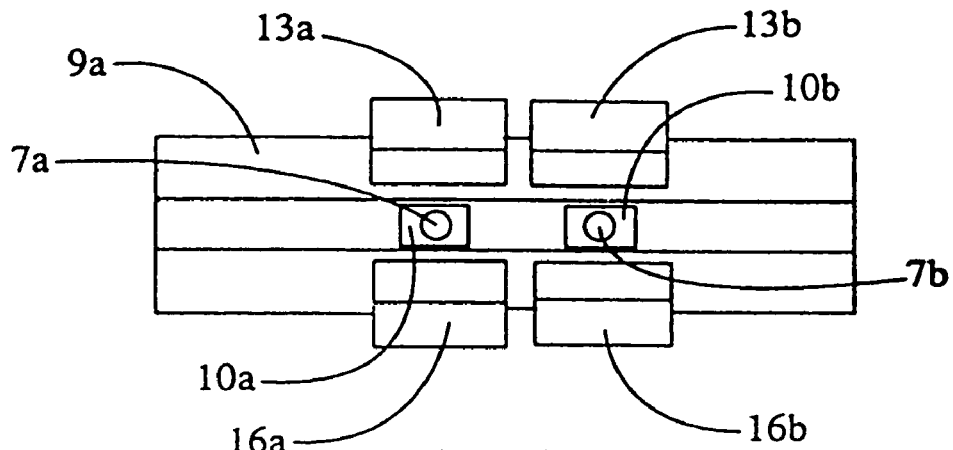
FIG. 4b is a top view of the multimode photometer depicted in FIG. 3.
Figure 4C:
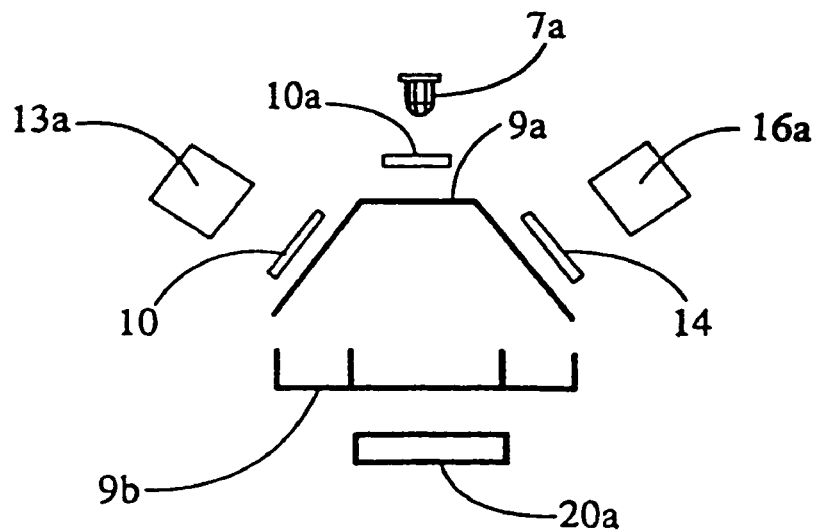
FIG. 4c is an exploded cross-sectional view of the components comprising the multimode photometer depicted in FIG. 3.

As prospectively illustrated in FIGS. 4a and 4b, there is shown different views of an optical tunnel equipped with two optical clusters as may be utilized for multispectral analysis. A light source 7 (LEDs 7a and 7b are shown) is positioned above an excitation filter 10 (filters 10a and 10b are shown) which in turn covers each excitation aperture (not shown). Two of four photodiodes 13a, 16a with filters 10, 14, as shown in the cross-sectional view of FIG. 4C, are mounted on the canopy 9a. A bar magnet 20a, as shown in FIG. 4C, is positioned at the base of the optical tunnel beneath each focal point 8 such that appropriate spectrophotometric analysis may be made at each location.

Although believed to be apparent from the foregoing discussion, there is provided herebelow a variety of examples by which the novel magnetic assays and methods of the present invention may be utilized in a variety of applications. As will be appreciated by those skilled in the art, for the purpose of discussion in the following examples the term "test solution" can mean test sample, test calibrator, or test control material.

EXAMPLE 1

A test strip is manufactured according to the description given in FIG. 1. The backing 4 is extended in length beyond the absorbent pad 3 end to allow application of bar codes, fluorescent markings, and other indicators to the backing 4. Reagent zone 2 contains streptavidin conjugated magnetic particles, buffers, stabilizers, surfactants, and other reagents in dry form.

The test strip 11 is inserted absorbent pad 3 end first into the optical tunnel 9. Indicators on the test strip are interpreted as calibration information by the analyzer. For example, the analyzer verifies that the same bar code was read at both focal points 8a and 8b and stores reflectance and fluorescence values for photodetectors 13 and 16. The calibration information and measured values are used by the analyzer to verify the quality and structure of an individual capture line as well as the amount of analyte, control, or calibrator present at the capture line, and to verify the performance of each optical module.

In a separate container the operator adds a measured volume of sample to a measured volume of test reagents and mixes them to form a reaction mixture. The test reagents include biotin conjugated anti-beta HCG, and fluorescent microsphere conjugated anti-alpha HCG which cooperatively bind HCG molecules present in the sample.

A measured volume of this reaction mixture is applied to the test strip reagent zone 2 it forms a new reaction mixture which contains magnetic particles in suspension as buffers, stabilizers, surfactants, and other reagents previously dried on the reagent zone 2. The magnetic particles bind the biotin conjugate in all of its complexed forms including those which have formed a cooperative complex (sandwich assay) with HCG and the anti-alpha HCG conjugate. Thus, fluorescent microspheres are indirectly bound to magnetic particles in proportion to the amount of analyte present in the reaction mixture.

As the magnetic particles suspended in the reaction mixture flow laterally within the plane of the test strip 11 they encounter a magnetic field applied using a bar magnet 20 attached to the base 9b of the optical tunnel 9. The applied magnetic field attracts the magnetic particles forming a magnetic barrier that selectively retains the magnetic particles at the focal point 8 while allowing reaction mixture to continue to flow laterally across this barrier toward the absorbent pad 3.

A measured volume of wash solution can also be added subsequent to the addition of reaction mixture. This will reduce the amount of fluorescent microspheres retained by the test membrane 1 and magnetic particles due to non-specific binding.

The analyzer monitors and compares photodetectors 16a and 16b measuring reflectance at the focal point 8a and 8b. The reflected light intensity at the focal point 8a decreases as the magnetic particles are retained by the magnet 20. The reflected light intensity at focal point 8b is a background (blank) measurement used to correct for differences between individual test strips and sample matrix effects. This allows the analyzer to determine whether the magnetic particles have been properly captured at focal point 8a, and to reject samples which are hemolyzed or contain elevated amounts of chromophores such as bilirubin. If the reflected light intensity is not within specification at focal points 8a and 8b during a predefined elapsed time the test is determined invalid and no result is reported.

Alternating with photodetectors 16a and 16b, the analyzer also monitors and compares photodetectors 13a and 13b measuring fluorescence. The emitted light intensity at focal point 8b is a background (blank) measurement used to correct for non-specific binding, differences between individual test strips, and sample matrix effects. The analyzer compares the blank emission measurement at 8b and test emission measurement at 8a and calculates HCG concentration.

EXAMPLE 2

Example 2 mirrors Example 1 but for the following differences:

Reagent zone 2 contains all test reagents prepackaged in unit dose dried form including: streptavidin conjugated magnetic particles, biotin conjugated anti-beta HCG, and fluorescent microsphere conjugated anti-alpha HCG which cooperatively bind HCG molecules present in the sample. Reagent zone 2 also contains buffers, stabilizers, surfactants, and other reagents in dry form.

The operator adds a measured volume of test solution directly to reagent zone 2.

EXAMPLE 3

Example 3 mirrors Example 2 but for the following differences:

Anti-alpha HCG is conjugated using alkaline phosphatase, instead of fluorescent micro spheres.

A measured volume of fluorescent substrate is added to the reagent zone 2 subsequent to the addition of a measured volume of wash solution.

EXAMPLE 4

Example 4 mirrors all of the above examples but for the following differences:

Example 4 substitutes a reagent pad 5 for reagent zone 2 in each of the preceding examples.

EXAMPLE 5

A test strip is manufactured according to the prescription given in FIG. 1. The backing 4 is extended in length beyond the absorbent pad 3 end to allow application of bar codes, fluorescent markings, and other indicators to the backing 4. Reagent zone 2 contains streptavidin conjugated magnetic particles, buffers, stabilizers, surfactants, and other reagents in dry form.

In a separate container, the operator adds a measured volume of test solution (containing cells, cell lysate, total RNA) to a measured volume of test reagents and mixes them to form a reaction mixture. The test reagents include biotinylated oligo (dT) probe and a 5' fluorescent dye labeled DNA hybridization probe specific for Chlamydia.

A measured volume of this reaction mixture is applied to the test strip reagent zone 2. As the reaction mixture comes in contact with the reagent zone 2 it forms a new reaction mixture which contains magnetic particles in suspension as well as buffers, stabilizers, surfactants, and other reagents previously dried in the reagent zone 2. the biotinylated oligo (dT) probe hybridizes specifically to the 3' poly(A) region of all mRNA present in the test solution. Consequentially, all mRNA is bound to the magnetic particles via a biotin/streptavidin bond. Labeled hybridization probe, in contrast, binds only target mRNA. The magnetic particles bind the biotinylated oligo (dT) probe in all of its complexed forms including those which have formed a cooperative complex (hybrid) with Chlamydia mRNA and the fluorescent dye labeled DNA hybridization probe specific for Chlamydia. Thus, fluorescent dye is indirectly bound to magnetic particles in proportion to the amount of Chlamydia mRNA present in the reaction mixture.

As the magnetic particles suspended in the reaction mixture flow laterally within the plane of the test strip 11 they encounter a magnetic field applied using a bar magnet 20 attached to the base 9b of the optical tunnel 9. The applied magnetic field attracts the magnetic particles forming a magnetic barrier that selectively retains the magnetic particles at the focal point 8 while allowing reaction mixture to continue to flow laterally across this barrier toward the absorbent pad 3.

A measured volume of wash solution can also be added subsequent to the addition of reaction mixture. This will reduce the amount of labeled DNA probe retained by the test membrane 1 and magnetic particles due to non-specific binding.

The analyzer monitors and compares photodetectors 16a and 16b measuring reflectance at the focal point 8a and 8b. The reflected light intensity at the focal point 8a decreases as the magnetic particles are retained by the magnet 20. The reflected light intensity at focal point 8b is a background (blank) measurement used to correct for differences between individual test strips and sample matrix effects. This allows the analyzer to determine whether the magnetic particles have been properly captured at focal point 8a, and to reject samples which are hemolyzed or contain elevated amounts of chromophores such as bilirubin. If the reflected light intensity is not within specification at focal points 8a and 8b during a predefined elapsed time the test is determined invalid and no result is reported. Alternating with photodetectors 16a and 16b, the analyzer also monitors and compares photodetectors 13a and 13b measuring fluorescence. The emitted light intensity at focal point 8b is a background (blank) measurement used to correct for non-specific binding, differences between individual test strips, and sample matrix effects. The analyzer compares the blank emission measurement at 8b and test emission measurement at 8a and calculates Chlamydia concentration or determines simply if Chlamydia is present in the test solution.

EXAMPLE 6

Other detection methods can be used with magnetic chromatography. In this example, x-ray film is used to detect the presence of target DNA in a population of transfected cells. PCR amplification of CDNA present in each test solution is accomplished using P32 labeled nucleotides. Amplified DNA is hybridized using 5' biotin DNA hybridization probe forming a reaction mixture which is applied to the test strip reagent zone 2 containing streptavidin conjugated magnetic particles.

Utilizing a test strip of the variety depicted in FIG. 5b, a wash solution is applied to reagent zone 2 subsequent to application of the reaction mixture.

A sheet of x-ray film is placed on top of said test strip array and exposed for a suitable length of time.

A visible band is seen on the developed x-ray film whose position corresponds with a sample which has tested positive for the target DNA.

EXAMPLE 7

Example 7 mirrors Example 6 but for the following differences:

Said PCR amplification is accomplished using 5' fluorescent dye labeled primer.

Said test strip array is positioned within a fluorescent scanner.

Said fluorescent scanner detects a fluorescent band whose position corresponds with a sample testing positive for the target DNA.

EXAMPLE 8

Example 8 mirrors Example 1 but for the following differences:

Said backing 4 is a microscope slide.

Said magnet 20 is positioned above said test membrane 1, so that magnet 20 is not in contact with test membrane 1.

A fluorescent microscope is used to count individual fluorescent microspheres bound to magnetic particles.

EXAMPLE 9

A test strip is manufactured according to the description given in FIG. 1. The backing 4 is extended in length beyond the absorbent pad 3 end to allow application of bar codes, fluorescent markings, and other indicators to the backing 4. Reagent zone 2 contains streptavidin conjugated 0.86 micron magnetic particles, anti-mouse IgG conjugated 150 nm magnetic particles, buffers, stabilizers, surfactants, and other reagents in dry form.

The test strip 11 is inserted absorbent pad 3 end first into the optical tunnel 9. Indicators on the test strip are interpreted as calibration information by the analyzer. For example, the analyzer verifies that the same bar code was read at both focal points 8a and 8b and stores reflectance and fluorescence values for photodetectors 13 and 16. The calibration information and measured values are used by the analyzer to verify the quality and structure of an individual capture line as well as the amount of analyte, control, or calibrator present at the capture line, and to verify the performance of each optical module.

In a separate container the operator adds a measured volume of sample to a measured volume of test reagents and mixes them to form a reaction mixture. The test reagents include biotin conjugated goat anti-beta FSH, and fluorescent microsphere conjugated goat anti-alpha FSH which cooperatively bind FSH molecules present in the sample. The test reagents also include mouse anti-beta LH, and fluorescent microsphere conjugated goat anti-alpha LH which cooperatively bind FSH molecules present in the sample.

A measured volume of this reaction mixture is applied to the test strip reagent zone 2. As the reaction mixture comes in contact with the reagent zone 2 it forms a new reaction mixture which contains 0.86 micron and 150 nm magnetic particles in suspension as well as buffers, stabilizers, surfactants, and other reagents previously dried on the reagent zone 2. The 0.86 micron magnetic particles bind the biotin conjugate in all of its complexed forms including those which have formed a cooperative complex (sandwich assay) with FSH and the anti-alpha FSH conjugate. Thus fluorescent microspheres are indirectly bound to magnetic particles in proportion to the amount of analyte present in the reaction mixture. The 150 nm magnetic particles bind the mouse anti-beta LH conjugate in all of its complexed forms including those which have formed a cooperative complex (sandwich assay) with LH and the goat anti-alpha LH conjugate. Thus, fluorescent microspheres are indirectly bound to magnetic particles in proportion to the amount of analyte present in the reaction mixture.

As the magnetic particles suspended in the reaction mixture flow laterally within the plane of the test strip 11 they encounter a first magnetic field applied using a bar magnet 20a attached to the base 9b of the optical tunnel 9. The applied magnetic field is of sufficient strength that it provides a magnetic barrier that selectively retains the 0.86 micron magnetic particles at the focal point 8a while allowing reaction mixture including 150 nm magnetic particles in suspension to continue to flow lateral across this barrier toward the absorbent pad 3.

As the 150 nm magnetic particles suspended in the reaction mixture flow laterally within the plane of the test strip 11 they encounter a second magnetic field applied using a second bar magnet 20b (not shown) attached to the base 9b of the optical tunnel 9. The second applied magnetic field is significantly stronger than said first applied magnetic field. This second applied magnetic field provides a magnetic barrier that selectively retains the 150 nm magnetic particles at the focal point 8b while allowing reaction mixture to continue to flow laterally across this second magnetic barrier toward the absorbent pad 3.

A measured volume of wash solution can also be added subsequent to the addition of reaction mixture. This will reduce the amount of fluorescent microspheres retained by the test membrane 1 and magnetic particles due to non-specific binding.

The analyzer monitors and compares photodetectors 16a and 16b measuring reflectance at the focal point 8a and 8b. The reflected light intensity at the focal point 8a decreases as the magnetic particles are retained by the first magnet 20a and second magnet (not shown). The reflected light intensity at focal points 8a and 8b are measurements used to determine whether the magnetic particles have been properly captured at focal points 8a and 8b. If the reflected light intensity is not within specification at focal point 8a and 8b during a predefined elapsed time the test is determined invalid and no result is reported.

Alternating with photodetectors 16a and 16b, the analyzer also monitors and compares photodetectors 13a and 13b measuring fluorescence. The emitted light intensity at focal points 8a and 8b are used to calculate FSH and LH concentrations respectively. The analyzer compares these emitted light intensities with those of test solutions containing known concentrations of FSH and LH, based upon such parameters, and calculates FSH and LH concentrations. It is to be further understood that various additions, deletions, modifications and alterations may be made to the above-described embodiments without departing from the intended spirit and scope of the present invention. In this regard, it should expressly be recognized that in addition to the magnetically-generated capture lines formed herein, additional capture lines may be formed as per conventional test strip assays which incorporate the use of bound receptors formed upon a test membrane.

EXAMPLE 10

A test strip is manufactured according to the description given in FIGS. 7a and 7b. The backing 4 is formed from a microscope slide. The lateral flow mesh 34 (chromatographic medium or stationary phase) consists of a 105 micron pore size mesh constructed from woven nylon fiber. The edges of the respective mesh 32, 34 are adhered to the microscope slide backing 4 using any suitable adhesive tape. This creates an adhesive free zone and allows the lateral flow mesh 34 to make direct contact with the microscope slide backing 4. The well 36 is mounted concentric with the respective mesh 32, 34 using any suitable adhesive or any other mechanical means which does not interfere with bilateral flow B of the test solutions. The absorbent pads 3', 3" are of approximately equal dimensions having a total absorbent capacity greater than the combined volumes of liquid reagents, test solutions, wash solutions and the like. As illustrated in FIGS. 7a and 7b, both absorbent pads 3', 3" are in fluid contact with the lateral flow mesh 34.

In a separate container, the operator may add a measured volume of test solution (e.g., peripheral blood or bone marrow suspected of containing cancer cells) to a measured volume of test reagents and mixes them to form a reaction mixture (mobile phase). If desired, common laboratory procedures may be used to remove the red blood cells from the test solution prior to mixing with the test reagents. The test reagents may comprise magnetic particles conjugated using antibodies specific for at least one human cancer cell type. These antibodies bind to the targeted cancer cell type(s) to make them magnetic. Subsequently, a measured volume of fluorescent dye labeled antibodies specific for the same cancer cell type(s) are added to the same reaction mixture. These antibodies may bind to the remaining available sites on the cancer cell type(s) to make them fluorescent. Therefore, the reaction mixture contains cancer cell type(s) that have been rendered both magnetic and fluorescent.

The test strip is strategically placed above the bar magnet 30 such that an opening at the bottom of the well 36 is positioned above the bar magnet 30. In one embodiment of the present invention, the opening at the bottom of the well 36 is circumscribed entirely by the bar magnet 30. The reaction mixture is deposited into the well 36. Gravity subsequently causes the reaction mixture to descend through the well 36 along direction A until it comes in contact with the vertical mesh 32. Upon contacting the vertical mesh 32, the reaction mixture is forced through the pores within the vertical mesh 32 by a combination of capillary action and gravitational force. The reaction mixture may then contact the lateral flow mesh 34 which conveys the liquid reaction mixture in bilateral directions B', B" by the capillary action until said reaction mixture is absorbed by the absorbent pads 3', 3".

As the magnetic particles and magnetically labeled cells in the reaction mixture flow from the well 36 to the lateral flow mesh 34, they encounter a magnetic field that is applied via the bar magnet 30. The applied magnetic field forms a magnetic barrier that selectively retains a majority of the magnetic particles and magnetically labeled cancer cells within a narrow capture zone. The non-magnetic remainder of the reaction mixture may continue to flow bilaterally B across this barrier to the absorbent pads 3', 3".

Subsequent to the addition of the reaction mixture, a volume of wash solution may be deposited in the well 36 while the test strip remains in position over the bar magnet 30. The magnetically labeled target cells and magnetic particles will remain held by the magnetic barrier while the non-target cells and unbound fluorescent antibodies are washed from the capture zone.

By utilizing the method above, over 100 million cells may be applied to a single microscope slide. Such method reduces the number of images that must be generated and examined from 48,000 to less than 40. Those of ordinary skill in the art will immediately recognize the advantage of capturing the cells directly on the slide, such that no cells may be lost during a transfer step which is known to be a crucial defect of prior art cell examination techniques.

EXAMPLE 11

Example 11 mirrors Example 10 but for the following differences:

A test strip is manufactured according to the description given in FIG. 7. The backing 4 is formed from a microscope slide that has been fabricated using an optically clear plastic such as polycarbonate or acrylic. The chromatographic medium or stationary phase 34 consists of a texture that is formed directly on the top surface of the microscope slide during the fabrication process (e.g.; injection molding, hot stamping, or casting). The texture can take any form suitable to achieve lateral flow of test solutions and reagents by capillary force.

It is to be understood and appreciated that various additions, deletions, modifications and alterations may be made to the above-described embodiments without departing from the intended spirit and scope of the present invention. In this respect, while various preferred embodiments of the present invention have been illustrated by means of specific examples, particularly with respect to magnetically-generated capture lines and techniques, is to be understood that the present invention is in no way to be deemed limited thereto. Accordingly, it is intended that all additions, deletions, modifications and alterations be included within the scope of the following claims.

The invention claimed is:

1. A multi-conformable assay system for use in performing a magnetic chromatography method, the assay comprising:
   (a) a microscope slide;
   (b) a housing positionable upon said microscope slide, said housing having a sample well formed thereon for receiving a reaction mixture having a quantity of magnetic particles suspended therein, said sample well tapered to have an opening;
   (c) at least one absorbent member positionable within said housing and adjacent to said sample well to absorb a portion of said reaction mixture deposited in said sample well not containing said magnetic particles; and (d) a layer of gel formed upon said microscope slide and aligned with said opening formed on said sample well, said layer of gel being operative to receive and contact said reaction mixture deposited through said sample well, wherein said gel comprises at least one digestive enzyme operative to react with a protein present within said reaction mixture.

2. The assay of claim 1 wherein said housing comprises a generally block-like structure defining an upper platform surface, said sample well being formed in the general midsection of said upper platform surface, said housing further defining first and second voids on opposed sides of said sample well; said system further comprising first and second absorbent pads, said first and second absorbent pads being received into dedicated ones of said voids of opposed sides of said sample well.

3. The assay of claim 2 wherein said housing is fabricated from a rigid, black material selected from the group consisting of plastic and metal.

4. The assay of claim 1 wherein said gel includes at least one receptor operative to bind with at least one of said magnetic particles of said reaction mixture.

5. The assay of claim 1 further comprising a magnet positionable below the microscope slide, wherein the magnet is alignable with said opening formed on said sample well.

6. A multi-conformable assay system for use in performing a magnetic chromatography method, the assay comprising:
   (a) a microscope slide;
   (b) a housing positionable upon said microscope slide, said housing having a sample well formed thereon for receiving a reaction mixture having a ciuantity of magnetic particles suspended therein, said sample well tapered to have an opening;
   (c) at least one absorbent member positionable within said housing and adjacent to said sample well to absorb a portion of said reaction mixture deposited in said sample well not containing said magnetic particles;
   (d) a layer of mesh formed upon said microscope slide, said layer of mesh defining a target area for receiving said reaction mixture as deposited through said sample well; and
   (e) a layer of gel formed upon said mesh alignable with said opening formed on said sample well such that said reaction mixture is contacted with said gel and deposited through said sample well, wherein said gel comprises at least one digestive enzyme operative to react with a protein present within said reaction mixture.

7. The assay of claim 6 wherein said housing is detachable from said absorbent pads, mesh and said microscope slide.

8. The assay of claim 6 wherein said housing and said absorbent pads are removable from said mesh and said microscope slide.

9. The assay of claim 8 wherein said mesh is removable from said microscope slide base.

10. The assay of claim 6 wherein said housing comprises a generally block-like structure defining an upper platform surface, said sample well being formed in the general midsection of said upper platform surface, said housing further defining first and second voids on opposed sides of said sample well; said system further comprising first and second absorbent pads, said first and second absorbent pads being received into dedicated ones of said voids of opposed sides of said sample well.

11. The assay of claim 10 wherein said housing is fabricated from a rigid, black material selected from the group consisting of plastic and metal.

12. The assay of claim 6 wherein said gel includes at least one receptor operative to bind with at least one of said magnetic particles of said reaction mixture.

13. The assay of claim 6 further comprising a magnet positionable below the microscope slide, wherein the magnet is alignable with said opening on said sample well.

* * * * *